(12) United States Patent
Hoshino et al.

(10) Patent No.: US 6,869,773 B2
(45) Date of Patent: Mar. 22, 2005

(54) PROCESS FOR THE MANUFACTURE OF CAROTENOIDS AND BIOLOGICALLY USEFUL MATERIALS THEREOF

(75) Inventors: Tatsuo Hoshino, Kamakura (JP); Kazuyuki Ojima, Fujisawa (JP); Yutaka Setoguchi, Fujisawa (JP)

(73) Assignee: DSM Nutritional Products, Inc., Parsippany, NJ (US)

( * ) Notice: Subject to any disclaimer, the term of this patent is extended or adjusted under 35 U.S.C. 154(b) by 363 days.

(21) Appl. No.: 09/727,855

(22) Filed: Dec. 1, 2000

(65) Prior Publication Data

US 2002/0168703 A1 Nov. 14, 2002

(30) Foreign Application Priority Data

Dec. 1, 1999 (EP) .............................. 99123821

(51) Int. Cl.⁷ ............................ C12N 1/20; C12N 1/14; C12P 23/00; C07H 21/04
(52) U.S. Cl. ................. 435/67; 435/252.3; 435/252.35; 435/254.11; 435/254.4; 435/320.1; 435/6; 435/189; 536/23.1; 536/23.2; 536/23.74
(58) Field of Search ....................... 435/67, 189, 252.3, 435/254.11, 254.4, 6, 252.35, 320.1, 254.1; 536/23.1, 23.2, 23.74

(56) References Cited

U.S. PATENT DOCUMENTS 6,696,293 B2 * 2/2004 Hoshino et al. ............ 435/440

FOREIGN PATENT DOCUMENTS

| EP | 0 769 551 A1 | 4/1997 |
| JP | 10-248575 | 10/1998 |
| WO | WO 90/02804 | 3/1990 |
| WO | WO 94/06918 | 3/1994 |
| WO | WO 97/263633 | 7/1997 |
| WO | WO 00/28041 | 5/2000 |

OTHER PUBLICATIONS

Schroeder, et al., "Antioxidant role of earotenoids in *Phaffia rhodozymo*," *Journal of General Microbiology*, vol. 139, pp. 907–912 (1993).

Derwent English Language Abstract of JP 10–248575 (document B3).

Wery. J. et al., "Structural and Phylogenetic Analysis of the Actin Gene from the Yeast *Phaffia rhodozyma*," *Yeast*, vol. 12, pp. 641–651 (1996).

Wery. J. et al., "High copy number integration into the ribosomal DNA of the yeast *Phaffia rhodozyma*," *Gene*, 184, pp. 89–97 (1997).

Shimda, II. et al., "Increased Carotenoid Production by the Food Yeast *Candida utilis* through Metabolic Engineering of the Isoprenoid Pathway," *Appl. & Env. Microbiol*, vol. 64, No. 7, pp. 2676–2680 (1998).

Croxen. R. et al., "Isoloation of an *Usulago maydis* gene encoding 3–hydroxy–3–methylglutaryl–coenzyme A reductase and expression of a C–termianl–truneated form in *Eschericia coli*," *Microbiology*. vol. 140, pp. 2363–2370 (1994).

(List continued on next page.)

*Primary Examiner*—Nashaat T. Nashed
(74) *Attorney, Agent, or Firm*—Bryan Cave LLP

(57) ABSTRACT

A process is provided for producing a carotenoid, which process includes cultivating a recombinant organism having a gene for one or more active oxygen species-quenching factor(s) that is substantially disrupted with a disruption cassette specific to the gene, and recovering carotenoids from the culture.

34 Claims, 1 Drawing Sheet

OTHER PUBLICATIONS

Martinez. C. et al., "Genetic transformation of astaxanthin of *Phaffia rhodozyma*," *Antonic van Leeowenhock*, vol. 73, pp. 147–153 (1998).

An. "Photosensitization of the Yeast *Phaffia rhodozyma* at a Low Temperature for Screening Carolenoid Hyperproducing Mutants," *Applied Biochemistry and Biotechnology*, vol. 66, pp. 263–268 (1997).

Shaish, et al., "Are active oxygen species involved in induction of B–carotene in *Dunaliella bardawil*" *Planta.* vol. 190. No. 3. pp. 363–368 (1993).

Schroeder, et al., "Singlet Oxygen and Peroxyl Radicals Regulate Carotenoid Biosynthesis in *Phaffia rhodoxyma*," *J. Biol. Chem.*, vol. 270. No. 31. pp. 18374–18379 (1995).

Cortez. et al., "Molecular Cloning and Expression Analysis of the *Rhodobacter capsulantus sod*BGene, Encoding an Iron Superoxide Dismutase," *Journal of Bacteriology*, vol. 180, No. 20, pp. 5413–5420 (1998).

Jakopitsch. et al., "Catalase–Peroxidase from the Cyanobacterium *Synechocystis* PCC 6803: Cloning, Overexpression in *Escherichia coli*, and Kinetic Characterization," *Biol. Chem.* vol. 380, pp. 1087–1096 (1999).

Forkl. et al., "Molecular clonging, sequence analysis and expression of the gene for catalase–peroxide (cpeA) from the photosynthetic bacterium *Rhodohacier copsulatus* B10," *Eur. J. Biochem.*, vol. 214, pp. 251–258 (1993).

Chung, et al., "Duplicate genes for Fe–containing superoxide dismutase in *Strepomyces coelicolor* A3(2)," *Gene*, vol. 231, pp. 87–93 (1999).

Creissen, et al., "Simultaneous targeting of pea glutathione reductase and of a bacterial fusion protein in chloroplasts and mitochondria in transgenic tobacco," *The Plant Journal*, vol. 8(2), pp. 167–175 (1995).

Lin, et al., "Cloning and Characterization of a cDNA for Manganese Superovide Dismutase from Callus of Sweet Potato," *J. Agric. Food Chem,.* vol. 45, pp. 521–525 (1997).

Neuport, "Protein Import Into Mitochondria," *Annu. Rev. Biochem.*, vol. 66, pp. 863–917, (1997).

Zhang, et al., "Photosenitisation Properties of Minochondrially I ocalised Green Fluorescent Protein," *Biochemical and Biphysical Research Communications.* vol. 242, pp. 390–395 (1998).

* cited by examiner

PROCESS FOR THE MANUFACTURE OF CAROTENOIDS AND BIOLOGICALLY USEFUL MATERIALS THEREOF

FIELD OF THE INVENTION

The present invention relates to the recombinant production of carotenoids, particularly astaxanthin, and to biologically useful materials therefor.

BACKGROUND OF THE INVENTION

Astaxanthin is known to be distributed in a wide variety of organisms, such as animals (e.g. birds such as flamingo and scarlet ibis, and fish such as rainbow trout and salmon), algae and microorganisms. It is also recognized that astaxanthin has a strong antioxidation property against active oxygen as well as most carotenoids. This property is expected to apply to the pharmaceutical usage of astaxanthin to protect living cells against some diseases, such as a cancer. Moreover, from the industrial application viewpoint, a demand for astaxanthin as a coloring reagent is increasing, especially in the farmed fish industry, such as salmon, because astaxanthin imparts distinctive orange-red coloration to the animals and contributes to consumer appeal in the marketplace.

*Phaffia rhodozyma* is known as a carotenogenic yeast strain that produces astaxanthin specifically. Different from the other carotenogenic yeast, *Rhodotorula*, *Phaffia rhodozyma* can ferment some sugars such as D-glucose. This is an important feature from an industrial application viewpoint. In a recent taxonomic study, a sexual cycle of *P. rhodozyma* was revealed and its telemorphic state was designated under the name of *Xanthophyllomyces dendrorhous* (W. I. Golubev; *Yeast* 11, 101–110, 1995). Some strain improvement studies to obtain hyper-producers of astaxanthin from *P. rhodozyma* have been conducted, however, in this decade, such effort have been restricted to employing the method of conventional mutagenesis and protoplast fusion. Recently, Wery et al. developed a host vector system using *P. rhodozyma* in which a non-replicable plasmid was used for multicopy integration onto the genome of *P. rhodozyma* at the ribosomal DNA locus (Wery et al., *Gene*, 184, 89–97, 1997). Verdoes et al. reported the use of improved vectors to obtain a transformant of *P. rhodozyma*, as well as its three carotenogenic genes which code the enzymes that catalyze the reactions from geranylgeranyl pyrophosphate to beta-carotene (International patent WO97/23633). The importance of genetic engineering methods to *P. rhodozyma* strain improvement studies should increase in the near future in order to surpass the productivity levels reached by conventional methods.

As described above, astaxanthin has an antioxidant property. This feature seems to have an important role in vivo for a protecting against active oxygen species such as $O_2.$, $H_2O_2$ and OH., which are continuously generated in living cells. An et al. obtained a hyperproducer of astaxanthin from *P. rhodozyma* by selecting for an antimycin-sensitive strain after conventional chemical mutagenesis (An, G-H. et al., *Appl. Env. Microbiol.*, 55 (1), 116–124, 1989). Antimycin is known to be an inhibitor of respiratory chain between cytochrome b and $C_1$ (Lucchini, G. et al., *Mol. Gen. Genet.*, 177, 139-, 1979) and such antimycin-sensitive mutants display enhanced pigmentation. Furthermore, active oxygen species produced due to a blockade of the primary respiratory chain at the $bc_1$ complex stimulated carotenoid formation (An, G-H et al., *Appl. Env. Microbiol.*, 55, 116–124, 1989). Indeed, addition of an $O_2.$ generator, duroquinone, to the growth medium increased total carotenoid content (the main carotenoid is astaxanthin) as well as the relative amounts of xanthophylls present in *P. rhodozyma*, while the active oxygen species-quenching factor mannitol reversed this effect (Schroeder, W. A. et al., *J. Gen. Microbiol.*, 139, 907–912, 1993). These results prompted the authors to speculate on the antioxidant property of astaxanthin in *P. rhodozyma*. In fact, astaxanthin production is stimulated in post-exponential growth phase when respiration activity is fully induced. Moreover, the addition of respiratory substrate, such as ethanol, to the medium enhanced astaxanthin production in *P. rhodozyma* (Gu, W-L. et al., *J. Ind. Microbiol. Biotechnol.*, 19, 114–117, 1997). Schroeder et al. tried to determine the relationship of the superoxide dismutase (SOD) and catalase activities, which act as native active oxygen species-quenching factors in *P. rhodozyma* to the productivity of astaxanthin, by comparing the difference between a parent strain and an antimycin-sensitive hyper-producer of astaxanthin. However, direct correlation of in vitro activity could not be observed.

SUMMARY OF THE INVENTION

In accordance with the present invention, the genes and the enzymes for active oxygen species-quenching factor(s), such as SOD and catalase are provided. SOD and catalase are biological materials that improve the carotenoid production process. This invention involves the cloning and the determination of the genes that code for mitochondrial and cytoplasmic SODs and catalases. This invention also involves enzymatically characterizing the result of disrupting these genes in *P. rhodozyma*. The disruption effects on the carotenogenesis can be confirmed by the cultivation of such transformants in an appropriate medium under an appropriate cultivation conditions.

More particularly, the present invention provides a process for producing carotenoids, which comprises cultivating a recombinant organism, whose gene for one or more active oxygen species-quenching factor(s) is substantially disrupted with the aid of a disruption cassette specific to the gene, and recovering carotenoids from the culture. The host organism of the recombinant organism may belong to the kingdom of *Monera, Protista* or *Fungi*. More preferably, the host organism of the recombinant organism may belong to the genus *Erwinia, Rhodobacter, Myxococcus, Flavobacter, Paracoccus, Synechococcus, Synechocystis, Agrobacterium, Streptomyces, Haematococcus, Dunaliella, Phaffia, Xanthophyllomyces, Neurospora, Rhodotorula, Blakeslea*, or *Phycomyces*. Most preferably, the host organism is a strain of *P. rhodozyma*.

The active oxygen species-quenching factor(s) is(are) mitochondrial superoxide dismutase (SOD), cytoplasmic superoxide dismutase (SOD), and/or catalase.

The present invention also provides a recombinant organism capable of producing carotenoids, characterized by the gene for at least one active oxygen species-quenching factor, that is substantially disrupted by introducing a disruption cassette specific to the gene. The active oxygen species-quenching factor(s) to be disrupted is(are) mitochondrial superoxide dismutase (SOD), cytoplasmic superoxide dismutase (SOD) and/or catalase.

As used herein, a polynucleotide or polypeptide sequence (A) is said to be substantially identical to another sequence (B) if sequence A is at least 75% identical, preferably 85% identical, such as at least 95% identical to sequence B.

Further, the present invention provides a recombinant DNA sequence coding for an active oxygen species-quenching factor effective in an organism capable of producing carotenoids. The DNA sequence is isolated from an organism belonging to the kingdom of *Monera, Protista* or *Fungi*, more preferably to the genus *Erwinia, Rhodobacter, Myxococcus, Flavobacter, Paracoccus, Synechococcus, Synechocystis, Agrobacterium, Streptomyces, Haematococcus, Dunaliella, Phaffia, Xanthophyllomyces, Neurospora, Rhodotorula, Blakeslea,* or *Phycomyces*. Particularly preferred organism is *P. rhodozyma*. The active oxygen species-quenching factor coded by the recombinant DNA sequence may be mitochondrial superoxide dismutase, cytoplasmic superoxide dismutase and/or catalase.

A recombinant DNA sequence coding for mitochondrial superoxide dismutase is identified by SEQ ID NO: 1 or 4, or it may have sufficiently high homology to the sequence of SEQ ID NO: 1 or 4 to hybridize under high stringency hybridization and wash conditions with either of the sequences of SEQ ID NOs: 1 and 4. A recombinant DNA sequence coding for cytoplasmic superoxide dismutase is identified by SEQ ID NO: 2 or 6, or it may have sufficiently high homology to the sequence of SEQ ID NO: 2 or 6 to hybridize under high stringency hybridization and wash conditions with either of the sequences of SEQ ID NOs: 2 and 6. Also a recombinant DNA sequence coding for catalase is identified by SEQ ID NO: 3 or 8, or it may have sufficiently high homology to the sequence of SEQ ID NO: 3 or 8 to hybridize under high stringency hybridization and wash conditions with either of the sequences of SEQ ID NOs: 3 and 8.

In the present invention, any combination of the following hybridization and wash conditions may be used, as appropriate, to identify homologous polynucleotide sequences:

High Stringency Hybridization:

6X SSC
  0.5% SDS
100 ug/ml denatured salmon sperm DNA
  50% formamide
Incubate overnight with gentle rocking at 42° C. overnight.
High Stringency Wash:

1 wash in 2X SSC, 0.5% SDS at Room Temperature for 15 minutes, followed by another wash in 0.1X SSC, 0.5% SDS at Room Temperature for 15 minutes.
Low Stringency Hybridization:

6X SSC
  0.5% SDS
100 ug/ml denatured salmon sperm DNA
  50% formamide
Incubate overnight with gentle rocking at 37° C. overnight.
Low Stringency Wash:

1 wash in 0.1X SSC, 0.5% SDS at Room Temperature for 15 minutes.

Moderately stringent conditions may be obtained by varying the temperature at which the hybridization reaction occurs and/or the wash conditions as set forth above.

Thus, as used herein, a sequence (A) is said to have "high homology" to another sequence (B) if sequence A hybridizes to sequence B under high stringency conditions (i.e., high stringency hybridization and wash conditions as defined above), and if the polypeptide or polypeptide fragment encoded by sequence A has the same activity as the polypeptide encoded by B.

The present invention further provides a recombinant DNA fragment that includes a coding region for a transit peptide upstream of the coding region of an objective protein, such as mitochondrial superoxide dismutase. The expression of this recombinant DNA fragment enables to locate the objective protein in mitochondria. Thus, the present invention also provides a method for locating an objective protein in mitochondria which comprises expressing the recombinant DNA fragment containing a coding region for a transit peptide located upstream of the coding region of an objective protein in an appropriate recombinant host organism.

As mentioned above, the present invention discloses the nucleotide sequences of active oxygen species-quenching factors, such as mitochondrial superoxide dismutase, cytoplasmic superoxide dismutase and catalase. These polynucleotides are provided for use as probes or primers for cloning the gene for active oxygen species-quenching factor (s) effective in other organisms capable of producing carotenoids, on the basis of the homology of the genes.

DETAILED DESCRIPTION OF THE INVENTION

Figure 1:
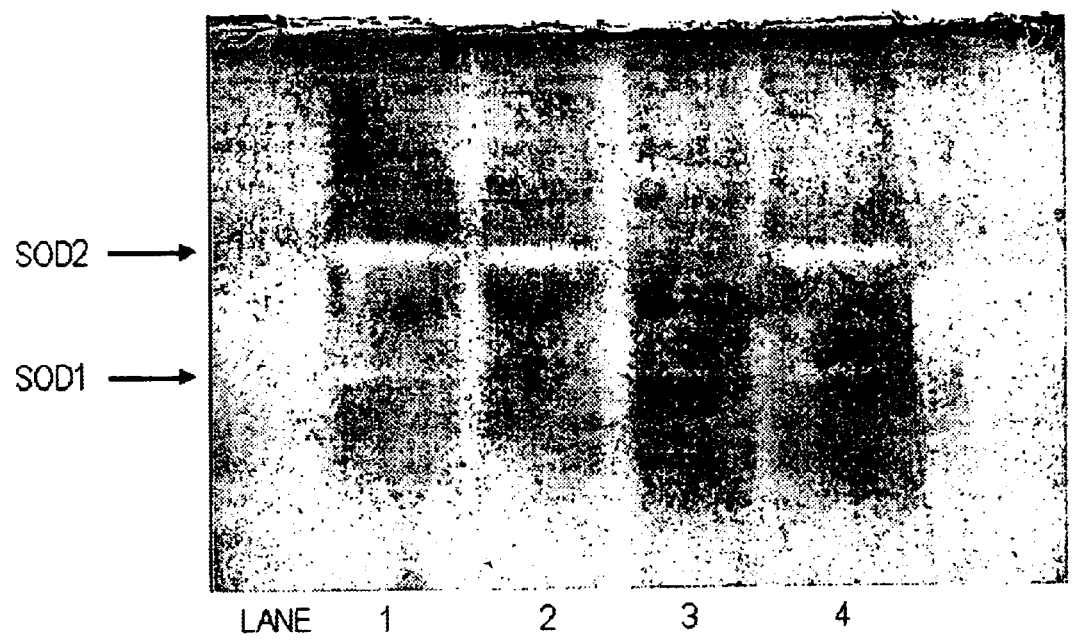
FIG. 1 shows activity staining for superoxide dismutase after native polyacrylamide gel electrophoresis by using cell-free extracts obtained from ATCC 96594 and its SOD mutants. Lane 1, *P. rhodozyma* ATCC 96594; Lane 2 *P. rhodozyma* ATCC 96594 :: pSOD/G717 (SOD1 disruptant); Lane 3 *P. rhodozyma* ATCC 96594 :: pSOD/G828 (SOD2 disruptant); Lane 4 *P. rhodozyma* ATCC 96594.

As noted above, one object of the present invention is to provide a novel process for producing carotenoids biologically. The novel process includes cultivating a recombinant organism whose gene for one or more active oxygen species-quenching factor(s) is substantially disrupted with the aid of a disruption cassette specific to the gene, and recovering carotenoids from the culture.

There is also provided a recombinant DNA sequences which contains an open reading frame coding for active oxygen species-quenching factor(s). Such a factor may be an enzyme, such as mitochondrial SOD or cytoplasmic SOD, or the recombinant DNA sequence may contain a partial fragment encoding a catalase gene. These sequences are useful for constructing the disruption cassette because they are able to recombine with the native gene(s) for the enzymes so as to specifically disrupt the gene(s).

The recombinant DNA sequence may be derived (i.e., isolated) from an organism belonging to the kingdom of *Monera, Protista* or *Fungi*, more preferably to the genus *Erwinia, Rhodobacter, Myxococcus, Flavobacter, Paracoccus, Synechococcus, Synechocystis, Agrobacterium, Streptomyces, Haematococcus, Dunaliella, Phaffia, Xanthophyllomyces, Neurospora, Rhodotorula, Blakeslea,* or *Phycomyces*. A particularly preferred organism is *P. rhodozyma*.

The active oxygen species-quenching factor coded by the recombinant DNA sequence may be mitochondrial SOD, cytoplasmic SOD and/or catalase. A specific example of a recombinant DNA sequence is derived from a gene of *Phaffia rhodozyma* and is selected from (i) a DNA sequence represented by SEQ ID NO: 1 or 2; (ii) those cDNAs identified by SEQ ID NO: 4 or 6; (iii) an isocoding or an allelic variant of the DNA sequence represented by SEQ ID NO: 1, 2, 4 or 6; and (iv) a derivative of a DNA sequence represented by SEQ ID NO: 1, 2, 4 or 6 with an addition, insertion, deletion and/or substitution of one or more nucleotide(s), and coding for a polypeptide having the enzyme activity. The recombinant DNA sequence may also be characterized as (a) coding for the enzyme having an amino acid sequence selected from the group of those described in SEQ ID NOs: 5 and 7, or (b) coding for a variant of the enzyme selected from (i) an allelic variant, and (ii) an enzyme having one or more amino acid addition, insertion, deletion and/or substitution and having the stated enzyme activity.

As used herein, an "allelic variant" means the variant that has at least one mutation in either one of two alleles in the diploid organism such as *Phaffa rhodozyma*, *Xanthophyllomyces dendrorhous* and the like. Both alleles of a given gene are concerned with the same trait or characteristic, but the product or function coded for by a particular allele differs, qualitatively and/or quantitatively, from that coded for by other alleles of that gene. Allelic variant can occur naturally or be generated artificially by means of chemical mutagenesis. A wild type allele is one which codes for a particular phenotypic characteristic found in the wild type strain of a given organism.

As used herein, an "isocoding variant" means the variant in which the nucleotide sequence of a given gene differs from the sequence from the wild type gene although its translated product (i.e. amino acid sequence) is identical with that from the wild type protein. This is caused by degeneracy of genetic code and by the difference of codon usage which is not identical among various organisms.

As used herein, a "derivative of a DNA sequence" is a DNA sequence that encodes a polypeptide having the activity of the corresponding SEQ ID NO but which differs from that DNA sequence by from 1–20, preferably 1–10, such as 1–5 nucleotide additions, insertions, deletions, and/or substitutions.

The specified recombinant DNA sequence mentioned above may be derived from a gene of *Phaffia rhodozyma* and is selected from (i) a DNA sequence represented by SEQ ID NO: 3; (ii) cDNA identified by SEQ ID NO: 8; (iii) an isocoding or an allelic variant of the DNA sequence represented by SEQ ID NO: 3 or 8; and (iv) a derivative of a DNA sequence represented by SEQ ID NO: 3 or 8 with additions, insertions, deletions and/or substitutions of one or more nucleotides, and coding for a polypeptide having the enzyme activity. The recombinant DNA sequence may also be characterized by (a) coding for the enzyme having a partial amino acid sequence selected from the group of those described in SEQ ID NO: 9, or (b) coding for a variant of the enzyme selected from (i) an allelic variant, and (ii) an enzyme having one or more amino acid additions, insertions, deletions and/or substitutions and having the stated enzyme activity. Such a recombinant DNA sequence may preferably be in the form of a vector.

The present invention also provides the use of the recombinant DNA sequence to transform a host organism to obtain an organism whose gene for at least one active oxygen species-quenching factor is substantially disrupted by introducing a disruption cassette specific to the gene. As used herein, a gene is "disrupted" or "substantially disrupted" if the activity of the polypeptide that it encodes is reduced relative to a non-disrupted gene. Preferably, the activity is reduced by 10%, preferably by at least 50% such as for example by at least 75%, more preferably by at least 90% to 100%.

A convenient form of the recombinant DNA sequence may be a vector. The recombinant organism obtained by use of the recombinant DNA is disrupted in its DNA sequence encoding mitochondrial SOD, cytoplasmic SOD, or catalase. The host organism transformed with the recombinant DNA is useful in improving the production process of carotenoids, in particular astaxanthin. Thus, the present invention also provides such a recombinant organism.

This biological production method of carotenoids may improve the productivity of carotenoids, in particular the productivity of astaxanthin. Thus, a method for producing a carotenoid is provided in which a recombinant microorganism as set forth above is cultivated under conditions conducive to the production of the carotenoid (see, e.g. the Examples) is one of the aspects of the present invention. This method may be applied to the biological production of astaxanthin.

Many researchers pointed out that active oxygen species might stimulate carotenoid production in known carotenogenic organisms. Carotenoid biosynthesis in cyst cells of *Haematococcus pluvialis* is enhanced by environmental oxidative stress (Kobayashi et al., Appl. Env. Microbiol., 59, 867–873, 1993). Carotenoid biosynthesis might be induced by active oxygen species and the accumulated carotenoids might function as a protective agent against oxidative stress damage in *Dunaliella bardawil* (Shaish et al., Planta, 190, 363–368, 1993). Although astaxanthin production in *P. rhodozyma* was studied in vivo under various cultivation conditions in which a generation of active oxygen species was altered, a correlation between active oxygen generated and carotenoids productivity was not clearly determined, probably because native active oxygen species-quenching factors were still present in such experiments and rescued the effects of active oxygen species on the carotenoid production to some extent (Schroeder, W. A. et al., J. Gen. Microbiol., 139, 907–912, 1993).

In this invention, to exclude the possibility that existence of native active oxygen species-quenching factor in *P. rhodozyma* can quench the positive effect by active oxygen on astaxanthin production, such native active oxygen species-quenching factors as SOD and catalase, were cloned from *P. rhodozyma* to disrupt their expression by constructing and introducing gene disruption plasmids. On the assumption that astaxanthin would play an antioxidant role in *P. rhodozyma*, inactivation of native active oxygen species-quenching factors may affect carotenoid production. This effect would probably occur because the relative increase in active oxygen species in vivo, due to absence of native active oxygen species-quenching factors, would stimulate a production of astaxanthin as an alternative agent for quenching active oxygen species.

Active oxygen species have toxicity to living cells because of the oxidative damage they cause to intercellular molecules, such as proteins or nucleic acids. Recent studies have revealed that aging is caused by oxidative damage by demonstrating a correlation between increased superoxide dismutase activity, increased life-span, and decreased oxidative damage in fruit flies and nematodes (Agarwal, S. et al., Proc. Natl. Acad. Sci. U.S A., 91, 12332–12335, 1994, Larsen, P. L., Proc. Natl. Acad. Sci. U.S. A., 90, 8905–8909, 1993, Sohal, R. S. et al., J. Biol. Chem., 270, 15671–15674, 1995). SOD and related antioxidant enzymes, and their genes, have been well studied in both prokaryotes and eukaryotes.

Yeast, such as *S. cerevisiae*, like most eukaryotes, contain Cu/ZnSOD (Product of the SOD1 gene) in the cytosol and MnSOD (product of the SOD2 gene) in the mitochondria. These enzymes catalyze the disproportionating of $O_2\cdot$, producing $O_2$ and $H_2O_2$. Together with small molecular antioxidants, such as glutathione and ascorbate, and other antioxidant enzymes, such as catalases and peroxidases; and metal chelating proteins such as metallothionein, they allow aerobes to survive under $O_2$, presumably by minimizing oxidative damage. The importance of cytoplasmic SOD was demonstrated by the high sensitivity to dioxygen shown by *S. cerevisiae* and *Escherichia coli* devoid of SOD. In both organisms, the loss of SOD activity was associated with slow growth in aerobic conditions, with higher mutation rates and specific biosynthetic defects. (sod1⁻ yeast requires lysine and methionine for aerobic growth, whereas sod-*E. coli* requires branched amino acids). In some cases, these effects are known to be due to the inhibitory effect of superoxide on iron sulfur cluster proteins (Gardner, P. R. et al., J. Biol. Chem., 266, 19328–19333, .1991, Kuo, C. F., et al., J. Biol. Chem., 262, 4724–4727, 1987). Mutants of sod2 of *S. cerevisiae* are little affected when grown in air with glucose as the carbon source. However, they are highly sensitive to hyperoxia and grow poorly in nomoxia, with carbon sources that require respiration for their metabolism.

Because genes coding for SOD and catalase have been cloned from other species, corresponding genes from *P. rhodozyma* can be cloned using the degenerate PCR method. At first, we cloned a partial gene fragment containing a portion of SOD gene and CAT gene by using the method set forth above. The degenerate PCR is a method to clone a gene of interest that displays high amino acid homology to the known enzyme of another species that has the same or similar function. The degenerate primer, which is used as a primer in degenerate PCR, was designed by reverse translation of the amino acid sequence of corresponding nucleotides ("degenerated"). In such a degenerate primer, a mixed primer which consists of any of A, C, G or T, or a primer containing inosine at an ambiguity code is generally used. In this invention, such mixed primers were used as degenerate primers for cloning the genes mentioned above. As described hereinafter, varied PCR conditions were used depending on the gene primers used for cloning. In this invention, two species of SOD genes, with sequences different from each other, were cloned from the same PCR band via degenerate PCR and named SOD1 and SOD2.

An entire gene containing its coding region and its intron, as well as its regulation region, such as a promoter or terminator, can be cloned from a chromosome by screening a genomic library with a partial DNA fragment obtained by degenerate PCR, as described above, as a probe after the probe is labeled. Generally, *E. coli* is used as a host strain and an *E. coli* vector, such as a λ phage vector or plasmid vector, such as a pUC vector, are often used in the construction of a library, following genetic manipulation such as sequencing, restriction digestion, ligation and the like. In this invention, an EcoRI genomic library of *P. rhodozyma* was constructed in the derivatives of λZAPII and λDASHII depending on an insert size. The insert size, in terms of the length of insert that must be cloned, was determined by Southern blot hybridization for each gene, prior to construction of a library. In this invention, the DNA was used as a probe was labeled with digoxigenin (DIG), a steroid hapten, instead of conventional $^{32}P$ label, following a protocol prepared by the supplier (Boehringer-Mannheim (Mannheim, Germany)). A genomic library constructed from the chromosome of *P. rhodozyma* was screened by using a DIG-labeled DNA fragment, which had a portion of a gene of interest, as a probe. Hybridized plaques were selected and used for further study. When λDASHII (insert size was from 9 kb to 23 kb), was used, the prepared λDNA was digested with EcoRI, followed by cloning of the EcoRI insert into a plasmid vector such as pUC19 or pBluescriptII SK+. When λZAPII was used in the construction of the genomic library, an in vivo excision protocol was conveniently used for the succeeding step of the cloning onto the plasmid vector with a derivative of a single stranded M13 phage, Ex assist phage (Stratagene, La Jolla, USA). Plasmid DNA thus obtained was examined for sequencing. In this invention, SOD1 and SOD2 genes were obtained from the λZAPII library independently from each other and catalase (CAT) gene was cloned from λDASHII library.

In this invention, we used the automated fluorescent DNA sequencer, ALFred system (Pharmacia, Uppsala, Sweden) using an autocycle sequencing protocol in which the Taq DNA polymerase is commonly employed for sequencing.

In this invention, the inventors determined the genomic sequence, containing an open reading frame of SOD1 gene or SOD2 gene, as well as its promoter and terminator sequences. From sequence analysis, it was found that SOD1 codes for a mitochondrial SOD, judged from the presence of a transit peptide at its amino terminal end. On the contrary, SOD2 does not have such a transit peptide sequence suggesting that SOD2 codes for a cytoplasmic SOD. The inventors also determined a partial genomic sequence of an open reading frame for the CAT gene.

A transit peptide is a signal sequence to transfer nucleic gene products that are encoded on a chromosome but whose translated proteins function in mitochondria, to the mitochondria, such as enzymes involved in the TCA cycle. To express some proteins in mitochondria, addition of a transit peptide t the protein's amino terminal end is useful.

In this invention, disruption plasmids for SOD1, SOD2 and CAT genes were constructed by ligating partial fragments of the above genes, which do not contain either end of the genes, to drug resistant genes, thus creating a suicide vector that cannot be autonomously replicated in *P. rhodozyma* due to lack of an autonomous replication sequence. A drug resistant gene that encodes an enzyme that enables the host to survive in the presence of a toxic antibiotic is often used as a selectable marker. A G418 resistance gene harbored in pPR2T (Verdoes et al. (International patent publication, WO97/23633)) is an example of a drug resistance gene. Such a suicide vector cannot replicate by itself and can be present only in an integrated form on the chromosome of the host as a result of a single-crossing recombination using the homologous sequence between the vector and the chromosome. In the case of recombination with a gene of interest, its genetic sequence cannot be reconstituted on the chromosome of the host strain due to the lack of either end of the gene. As a consequence, the gene of interest could be disrupted in the recombinant strain thus obtained.

Another example for disruption plasmid is a double crossing over type of plasmid. This type of disruption plasmid contains two different partial fragments of the objective gene to be disrupted and a selective marker gene, such as a drug resistant gene, is inserted between the two fragments. After recombination between the chromosome of the recipient cell and donor plasmid DNA at the two homologous parts of the gene, replacement of the chromosome sequence with the donor DNA occurs and a selective marker gene is inserted into the objective gene that is to be disrupted. In general, a double crossing over type of plasmid has a lower frequency of recombination than single crossing over type of vector.

In this invention, the enzymes of interest were inactivated by disrupting the corresponding genes. The other way to evaluate the effect of gene product of interest is to decrease its expression by genetic engineering methods. For this purpose, some methods were used. One such method is the anti-sense method. The anti-sense method is used to decrease the expression of a gene of interest by introducing an artificial gene fragment whose sequence is complementary to that of the gene of interest. Such an anti-sense gene fragment forms a complex with the mature MRNA fragment of the objective gene in vivo and as a consequence, inhibits the efficient translation of the MRNA.

Another method is a mutation of the promoter region. In general, a gene consists of several parts that have different functions from each other. In eukaryotes, genes that encode corresponding proteins are transcribed to premature messenger RNA (pre-mRNA), which differs from the genes for ribosomal RNA (rRNA), small nuclear RNA (snRNA), and transfer RNA (tRNA). Although RNA polymerase II (PolII) plays a central role in this transcription event, PolII cannot solely start transcription without a cis element covering an upstream region containing a promoter and an upstream activation sequence (UAS), and a trans-acting protein factor. At first, a transcription initiation complex, which consists of several basic protein components, recognize the promoter sequence in the 5'-adjacent region of the gene to be expressed. In this event, some additional participants are required in the case of a gene which is expressed under some specific regulation, such as a heat shock response, or adaptation to a nutritional starvation, and so on. In such a case, a UAS is required to exist in the 5'-untranslated upstream region around the promoter sequence, and some positive or negative regulator proteins recognize and bind to the UAS. The binding strength of the transcription initiation complex to the promoter sequence is affected by the binding of a trans-acting factor around the promoter, thus enabling the regulation of transcription activity.

After the activation of a transcription initiation complex by phosphorylation, the transcription initiation complex initiates transcription from the transcription start site. Some parts of the transcription initiation complex detach as an elongation complex and progress from the promoter region to the 3' direction of the gene (this step is called a promoter clearance event). The elongation complex continues transcription until it reaches a termination sequence that is located in the 3'-adjacent downstream region of the gene.

To decrease the expression of a gene of interest, mutation by conventional chemical mutagenesis or genetic site-directed mutagenesis in the promoter region of the objective gene containing a UAS sequence, as described above, is often used. Mutant strains in which the expression of an enzyme of interest might decrease can be obtained by transforming a host strain with recombinant DNA having such a mutated promoter region. As described above, such an attempt to decrease the expression of a gene, as well as gene disruption, are employed to determine the effect of a gene product on the phenomena of living organisms.

As a transformation method, LiCl method (Wery et al., *Yeast*, 12 (7), 641–651, 1996) and electroporation method (Wery et al., *Gene*, 184, 89–97, 1997) were applied to transform *P. rhodozyma*. However, the efficiency of transformation under these conditions seemed to be low. Thus, in this invention, the biolistic transformation method (Johnston et al., *Methods in Molecular Biology*, 53; 147–153, 1996) was used for the transformation of *P. rhodozyma*. The biolistic method is a simple and reliable protocol in which donor DNA coated on a gold or tungsten particle is shot into the living cells directly with high-pressured helium gas. This transformation protocol was successfully applied to *Cryptococcus neoformans*, which is a basidiomycetous yeast, as well as *P. rhodozyma*, and was difficult to transform with conventional transformation methods (Toffaletti, et al., *J. Bacteriol.*, 175 (5), 1405–1411, 1993). In this invention, this biolistic method was successfully used to transform *P. rhodozyma* cells.

The event of gene disruption can be confirmed by enzymatic characterization directly and by genetic analysis with PCR or Southern blot hybridization by using the chromosome obtained from transformants obtained as above. In this invention, the direct confirmation of SOD disruption was performed by activity staining. The characterization of catalase disruption was conducted by visual observation, such as the catalase test, which is often used in bacterial taxonomy.

Such a genetically engineered *P. rhodozyma* would be cultivated in an appropriate medium and evaluated for its productivity of astaxanthin.

The following materials and methods were employed in the Examples described below:

Strains

*P. rhodozyma* ATCC 96594 (re-deposited under the accession No. ATCC 74438 on Apr. 8, 1998 pursuant to the Budapest Treaty).

*E. coli* DH5: F$^-$, φ80d, lacZΔM15, Δ(lacZYA-argF)U169, hsd ($r_K^-$,$m_K^+$), recA1, endA1, deoR, thi-1, supE44, gyrA96, relA1 (Toyobo, Osaka, Japan).

*E. coli* XL1-Blue MRF': Δ(mcrA)183, Δ(mcrCB-hsdSMR-mrr)173, endA1, supE44, thi-1, recA1, gyrA96, relA1, lac[F' proAB, lacI$^q$ZΔM15, Tn10 (tet$^r$)] (Stratagene, La Jolla, USA).

*E. coli* SOLR: e14$^-$(mcrA), Δ(mcrCB-hsdSMR-mrr)171, sbcC, recB, recJ, umuC :: Tn5(kan$^r$), uvrC, lac, gyrA96, relA1, thi-1, endA1, λ$^R$, [F' proAB, lacI$^q$ZΔM15] Su$^-$ (nonsuppressing) (Stratagene).

*E. coli* XL1 MRA (P2): Δ(mcrA)183, Δ(mcrCB-hsdSMR-mrr)173, endA1, supE44, thi-1, gyrA96, relA1, lac (P2 lysogen) (Stratagene).

*E. coli* TOP10: F$^-$, mcrA, Δ(mrr-hsdRMS-mcrBC), φ80, ΔlacZ M15, ΔlacX74, recA1, deoR, araD139, (ara-leu)7697, galU, galK, rpsL (Str$^r$), endA1, nupG (Invitrogen, Carlsbad, USA).

Vector

λZAPII (Stratagene)

λDASHII (Stratagene)

pBluescriptII SK+(Stratagene)

pCR2.1TOPO (Invitrogen)

pUC19 (Takara Shuzo, Otsu, Japan)

Media

The *P. rhodozyma* strain is maintained routinely on agar plates of YPD medium (DIFCO, Detroit, USA). The *E. coli* strain is maintained in LB medium (10 g Bacto-trypton, 5 g yeast extract (DIFCO) and 5 g NaCl per liter). NZY medium (5 g NaCl, 2 g MgSO$_4$-7H$_2$O, 5 g yeast extract (DIFCO), 10 g NZ amine type A (WAKO, Osaka, Japan) per liter is used for phage propagation in soft agar (0.7% agar (WAKO)). When agar medium was prepared, 1.5%(wt) of agar (WAKO) was supplemented.

Methods

A general method of molecular genetic techniques was used, according to the method in Molecular cloning: a Laboratory Manual, 2nd Edition (Cold Spring Harbor Laboratory Press, 1989). Restriction enzymes and T4 DNA ligase were purchased from Takara Shuzo (Japan).

Isolation of a chromosomal DNA from *P. rhodozyma* was performed using QIAGEN Genomic Kit (QIAGEN, Hilden, Germany) following the protocol supplied by the manufacturer. Mini-prep isolation of plasmid DNA from transformed

*E. coli* was performed with the Automatic DNA isolation system (PI-50, Kurabo, Co. Ltd., Osaka, Japan). Midi-prep isolation of plasmid DNA from an *E. coli* transformant was performed using QIAGEN column (QIAGEN). Isolation of λ DNA was performed with Wizard lambda preps DNA purification system (Promega, Madison, USA) following the protocol supplied by the manufacturer. DNA fragments were isolated and purified from agarose using QIAquick or QIAEX II (QIAGEN). Manipulation of λ phage derivatives was conducted using the protocol supplied by the manufacturer (Stratagene).

Isolation of total RNA from *P. rhodozyma* was performed with the phenol method by using Isogen (Nippon Gene, Toyama, Japan). mRNA was purified from total RNA thus obtained using mRNA separation kit (Clontech, Palo Alto, USA). cDNA was synthesized using CapFinder cDNA construction kit (Clontech).

In vitro packaging was performed using Gigapack III gold packaging extract (Stratagene).

Polymerase chain reaction (PCR) was performed with the Perkin Elmer model 2400 thermal cycler. Each of the PCR conditions used is described in the examples below. PCR primers were purchased from a commercial supplier or synthesized with a DNA synthesizer (model 392, Perkin Elmer, Japan, Urayasu, Japan). Fluorescent DNA primers for DNA sequencing were purchased from Pharmacia. DNA sequencing was performed with the automated fluorescent DNA sequencer (ALFred, Pharmacia).

Competent cells of *E. coli* DH5α were purchased from Toyobo (Japan).

The apparatus and reagent for biolistic transformation of *P. rhodozyma* were purchased from Nippon Bio-Rad Laboratories (Tokyo, Japan).

The following examples are provided to further illustrate the process of the present invention. These examples are illustrative only and are not intended to limit the scope of the invention in any way.

EXAMPLES

Example 1

Isolation of mRNA from *P. rhodozyma* and Construction of a cDNA Library

To construct cDNA library of *P. rhodozyma*, total RNA was isolated by the phenol extraction method right after cell disruption, and the mRNA from *P. rhodozyma* ATCC 96594 strain was purified using an mRNA separation kit (Clontech).

Cells of the ATCC96594 strain from 10 ml of a two-day-culture in YPD medium were harvested by centrifugation (1500×g for 10 minutes) and washed once with extraction buffer (10 mM Na-citrate/HCl (pH 6.2) containing 0.7 M KCl ). After suspending in 2.5 ml of extraction buffer, the cells were disrupted using a French press homogenizer (Ohtake Works Corp., Tokyo, Japan) at 1500 kgf/cm² and immediately mixed with two volumes of isogen (Nippon gene) according to the method specified by the manufacturer. 400 µg of total RNA was recovered.

This total RNA was purified using an mRNA separation kit (Clontech) according to the method specified by the manufacturer. Finally, 16 µg of mRNA from *P. rhodozyma* ATCC 96594 strain was obtained.

To obtain cDNA species from *P. rhodozyma*, CapFinder PCR cDNA construction kit (Clontech) was used according to the method specified by the manufacturer. One µg of purified mRNA was applied for a first strand synthesis followed by PCR amplification. After this amplification by PCR, 1 mg of cDNA pool was obtained.

Example 2

Cloning of Two Species of Partial SOD Gene from *P. rhodozyma*

To clone a partial SOD gene from *P. rhodozyma*, a degenerate PCR method was used. The nucleotide sequences of two mixed primers were designed and synthesized as shown in TABLE 1 based on the common sequence of known superoxide dismutase genes from other species.

TABLE 1

Sequence of primers used in the cloning of SOD1 and SOD2 genes

|  |
|---|
| (SEQ ID NO: 10) |
| Sod1; AARCAYCAYCARACNTAYGTNAA (sense primer) |
| (SEQ ID NO: 11) |
| Sod4; GCCCANCCNGANCCYTGNACNCC (antisense primer) |

(R = A or G; Y = C or T; N = A, C, G or T)

After a PCR reaction of 25 cycles at 94° C. for 15 seconds, 46° C. for 30 seconds and 72° C. for 15 seconds, using ExTaq (Takara Shuzo) as a DNA polymerase and the cDNA pool obtained in Example 1 as a template, the reaction mixture was separated using agarose gel electrophoresis. A PCR band that had the desired length was recovered and purified by QIAquick (QIAGEN) according to the method of the manufacturer and then ligated to pCR2.1-TOPO (Invitrogen). After the transformation of competent *E. coli* TOP10, 6 white colonies were selected and plasmids were isolated with Automatic DNA isolation system (Kurabo PI-50). As a result of sequencing, it was found that two clones had different sequences from each other, and both amino acid sequences were independently similar to known SOD genes. These isolated cDNA clones were designated pSOD614 #2 and pSOD614 #3, and used for further study.

Example 3

Isolation of Genomic DNA from *P. rhodozyma*

To isolate a genomic DNA from *P. rhodozyma*, a QIAGEN genomic kit was used according to the method specified by the manufacturer.

Initially, cells of *P. rhodozyma* ATCC 96594 strain from a 100 ml overnight culture in YPD medium were harvested by centrifugation (1500×g for 10 minutes) and washed once with TE buffer (10 mM Tris/HCl (pH 8.0) containing 1 mM EDTA). After suspending in 8 ml of Y1 buffer of the QIAGEN genomic kit, lyticase (SIGMA) was added at the concentration of 2 mg/ml to disrupt cells by enzymatic degradation. The reaction mixture was incubated for 90 minutes at 30° C. and then continued on to the next extraction step. Finally, 20 µg of genomic DNA was obtained.

Example 4

Southern Blot Hybridization by using pSOD614 #2 and pSOD614 #3 as Probes

Southern blot hybridization was performed to clone genomic fragments that contain SOD genes from *P. rhodozyma*. Two µg of genomic DNA were digested by EcoRI and subjected to agarose gel electrophoresis followed by acidic and alkaline treatment. The denatured DNA was transferred to a nylon membrane (Hybond N+, Amersham) using transblot (Joto Rika, Tokyo, Japan) for an hour. The DNA was transferred to a nylon membrane and fixed by heat treatment (80° C., 90 minutes). Probes were prepared by labeling the template DNAs (EcoRI-digested pSOD614 #2 and pSOD614 #3) with the DIG multipriming method (Boehringer Mannheim). Hybridization was performed using the method specified by the manufacturer. As a result, hybridized bands were visualized at a of 7.5 kilobases (kb) against the probe prepared from pSOD614 #2, and at a length of 8.0 kilobases (kb) against the probe prepared from pSOD614 #3.

Example 5

Cloning of Genomic Fragments Containing SOD Genes Whose Sequences were Different from Each Other Four µg of the genomic DNA were digested by EcoRI and subjected to agarose gel electrophoresis. Then, DNAs whose length are within the range from 7 to 9 kb were recovered by a conventional elution method using a dialysis membrane. The purified DNA was ligated to 1 µg of EcoRI-digested and CIAP (calf intestine alkaline phosphatase)-treated λZAPII (Stratagene) at 16° C. overnight, and packaged with Gigapack III gold packaging extract (Stratagene). The $E.$ $coli$ XL1Blue MRF' strain was infected with the packaged extract and over-laid with NZY medium poured onto LB agar medium. About 6000 plaques were screened using EcoRI-digested pSOD614 #2 and pSOD614 #3 as probes. Six plaques were hybridized to the labeled pSOD614 #2 probe and two plaques were hybridized to the labeled pSOD614 #3 probe. Then, the hybridized plaques were subjected to an in vivo excision protocol according to the method specified by the manufacturer (Stratagene). As a result of PCR analysis using sod1 and sod4 primers, it was found that one plasmid isolated from the six pSOD614 #2-hybridized plaques had the same fragments as that of pSOD614 #2. This plasmid was named pSOD703. As a result of PCR analysis using sod1 and sod4 primers, it was also found that two plasmids isolated from the two of pSOD614 #3-hybridized plaques had the same fragment as that of pSOD614 #3. One of the plasmids was named pSOD626 and used for further study.

Example 6

Sequence Analysis of Two Species of MnSOD Genes Obtained from $P.$ $rhodozyma$

A complete nucleotide sequence was determined by sequencing of pSOD703 and pSOD626 with a primer-walking procedure. The nucleotide sequence and the deduced amino acid sequence for the SOD1 gene, which harbored on pSOD703, and for the SOD2 gene, which is harbored on pSOD626, are provided as SEQ ID NOs: 1, NO: 2, NO: 5 and NO: 7 herein.

Both of the deduced amino acid sequences of the SOD1 and SOD2 genes were homologous to known MnSODs obtained from other species, and not to Cu/ZnSODs or FeSOD as a result of BLAST analysis (Altschul, S. F. et al., $J.$ $Mol.$ $Biol.$ 215, 403–410, 1990).

The SOD1 gene had 7 introns and 8 exons. Its deduced open reading frame consisted of 223 amino acids. On the other hand, the SOD2 gene had 10 introns and 11 exons, and its deduced open reading frame consisted of 199 amino acids. Most of the differences between the two isolated SOD genes occurred in an extended region of the SOD1 gene at its amino terminal end, whose sequence might act as a transit peptide to mitochondria.

In fact, Schroeder et al. reported two species of SODs in $P.$ $rhodozyma$ which were detected as KCN- and $H_2O_2$-resistant SODs in the activity staining of native polyacrylamide gel electrophoresis (PAGE). They commented that two species of MnSOD were indicated as aggregates or isozymes, and they did not refer to the species' precise nature and their subcellular location. As described in the following section, it was clarified that two species of these KCN- and $H_2O_2$- resistant SODs (i.e. MnSOD) were products of the SOD1 and SOD2 genes. As described in the section of "Detailed Description of the Invention," most eukaryotes have different species of SODs located intracellularly (MnSOD in the mitochondrial fraction and Cu/ZnSOD in the cytoplasmic fraction). This is the first example in which two species of MnSODs have functioned in different subcellular locations.

Example 7

Construction of Disruption Plasmids for SOD1 and SOD2 Genes

As described in the section "Detailed Description of the Invention," a plasmid harboring a drug resistant marker cassette was constructed by inserting G418 resistant structural gene between the promoter and terminator genes of glyceraldehyde-3-phosphate dehydrogenase (GAP) and ligating thus into KpnI- and HindIII-digested pUC19. This plasmid was named pUC-G418 and used for further study. As gene fragments used for homologous recombination, partial fragments of the SOD1 and SOD2 genes were synthesized in vitro by the PCR method using PCR primers whose sequences were shown in TABLE 2.

TABLE 2

| | | |
|---|---|---|
| Sod14:; | GGTACCTCCGATGATAGGAATGTGAG (sense primer) | (SEQ ID NO: 12) |
| Sod15:; | GAATTCAGTTCAACGGAGGAGGACAC (antisense primer) | (SEQ ID NO: 13) |
| Sod47:; | GAATTCGGAGGAGGACACATCAACCG (sense primer) | (SEQ ID NO: 14) |
| Sod48:; | GGTACCTGTACTGGAGGTAGAAAGCG (antisense primer) | (SEQ ID NO: 15) |

PCR conditions were as follows: 25 cycles of 94° C. for 15 seconds, 50° C. for 30 seconds, and 72° C. for 15 minutes. As a template, 0.1 µg of genomic DNA obtained in Example 3 was used, and ExTaq was used as a DNA polymerase. A partial fragment of SOD1 which could be obtained from PCR using sod14 and sod15 as primers, and a partial SOD2 gene that could be obtained from PCR using sod47 and sod48 as primers, were amplified respectively. Amplified 0.65 kb fragments were recovered and cloned into pCR2.1-TOPO (Invitrogen) according to the protocol specified by the manufacturer. Six independent clones from white colonies of $E.$ $coli$ TOP10 transformants were selected, and plasmids were prepared from those transformants. As a result of restriction analysis and sequencing, one clone that had a partial SOD1 gene was selected for a further study and named pSOD715. In a similar manner, one clone that had a partial SOD2 gene was selected and named pSOD826.

Then, pSOD715 and pSOD826 were digested by EcoRI and KpnI, yielding 0.65 kb fragments that were purified using QIAquick protocol and ligated to EcoRI- and KpnI-digested pUC19-G418. Six independent clones from ampicillin-resistant colonies of *E. coli* DH5α transformants were selected and plasmids were prepared from those transformants. As a result of restriction analysis and sequencing, one clone in which a partial SOD1 was fused to the G418 resistant cassette was obtained and named pSOD/G717. In a similar manner, one clone in which a partial SOD2 was fused to the G418 resistant cassette was obtained and named pSOD/G828.

Example 8

Transformation of *P. rhodozyma* ATCC 96594 Using the Biolistic Method

Transformation protocols were followed according Methods in Molecular Biology (Johnston et al., 53; 147–153, 1996). As a host strain, *P. rhodozyma* ATCC 96594 was cultured in YPD medium to stationary phase. After centrifugation of the broth, cells were concentrated 10-fold with sterilized water. 200 µl of cell suspension were spread on YPD medium containing 100 µg of geneticin, and 0.75 M of mannitol and sorbitol. Five micrograms of the circular DNA of pSOD/G717 and pSOD/G828 were coated on 1.5 mg of 0.9 µm gold particles, and used as donor DNA for biolistic transformation. Hundreds of geneticin-resistant clones were obtained after one week of incubation at 20° C. Four of those transformants were selected and chromosomes were prepared from them. One of the transformants was confirmed to have this disrupted structure of chromosomal SOD1 or SOD2 genes by PCR and Southern blot hybridization analyses, and was used for further study.

Example 9

Activity Staining of Native PAGE Using Crude Extracts Obtained from Candidates for SOD1 and SOD2 Disruptants ATCC 96594 strain and candidates obtained from the biolistic transformation of ATCC 96594 were cultivated in YPD medium for two days and harvested by centrifugation for 10 minutes by 3000×g at 4° C. After washing with Tris-HCl buffer (10 mM/pH 8.0), cells were concentrated 10-fold with the same buffer. Cells were disrupted with a French press homogenizer (Ohtake Works) at 1500 kg/cm² and a crude extract was prepared after microcentrifugation at 15000 rpm (TOMY, MRX150) of homogenized fraction.

The protein concentration of the crude extract, thus prepared, was determined with BCA protein assay reagent manufactured by PIERCE (Rockford, U.S.A.). A volume of crude extract corresponding to 300 µg of protein was subjected to native PAGE according to the method described by Schroeder W. A. et al. (*J. Gen. Microbiol.*, 139, 907–912, 1993). Activity staining was conducted according to the method of Flohé et al. (*Methods in Enzymology*, 105, 93–104, 1984).

The results of the activity staining are depicted in FIG. 1. In the extract of parental strain, ATCC 96594, two bands were visualized as transparent bands that have SOD activity in the dark background. On the contrary, the ATCC 96594 :: pSOD/G717 strain, in which the SOD1 gene was disrupted, lacks an activity band with high mobility in native PAGE and ATCC 96594 :: pSOD/G828 strain, in which the SOD2 gene was disrupted lacks an activity band with low mobility in native PAGE. From this result, it was found that two species of MnSOD that were present in the crude extract of *P. rhodozyma* were the products of SOD1 and SOD2 genes, and the SOD species with high mobility and with low mobility in native PAGE corresponded to the SOD1 and SOD2 gene product, respectively.

Example 10

Cloning of the Partial Catalase (CAT) Gene from *P. rhodozyma*

To clone a partial CAT gene from *P. rhodozyma*, a degenerate PCR method was exploited. Two mixed primers were designed and synthesized as shown in TABLE 3 with their nucleotide sequences based on the common sequence of known catalase genes from other species.

TABLE 3

Sequence of primers used in the cloning of the CAT genes

|  |
| --- |
| (SEQ ID NO: 16) |
| Cat2: MGNTTYTCNACNGTNGGNGGNGA (sense primer) |
| (SEQ ID NO: 17) |
| Cat5: CKRTGNCKYTGNGTRTCNGGRTA (antisense primer) |

(M = A or C; N = A, C, G or T; Y = C or T; K = G or T; R = A or G)

After the PCR reaction of 25 cycles of 94° C. for 15 seconds, 45° C. for 30 seconds and 72° C. for 15 seconds, using ExTaq (Takara Shuzo) as a DNA polymerase and genomic DNA obtained in Example 3 as a template, the reaction mixture was applied to agarose gel electrophoresis. A PCR band of 1.0 kb length was recovered and purified by QIAquick (QIAGEN) according to the method of the manufacturer and then ligated to pCR2.1-TOPO (Invitrogen). After the transformation of competent *E. coli* TOP10, 6 white colonies were selected and plasmids were isolated with Automatic DNA isolation system. As a result of sequencing, it was found that two clones had sequence whose deduced amino acid sequences were similar to known CAT genes. One of these isolated DNA clones was designated as pCAT702 and used for further study.

Example 11

Cloning of Genomic Fragments Containing the CAT Gene

In a similar manner to Example 4, a Southern blot hybridization study was performed using pCAT702 as a probe. As a result, a hybridized band with a size from 9 kb to 23 kb was visualized. Next, 4 µg of the genomic DNA was digested by EcoRI and subjected to agarose gel electrophoresis. Then, DNAs whose length is within the range from 9 to 23 kb were recovered by a conventional elution method using a dialysis membrane. The purified DNA was ligated to 1 µg of EcoRI-digested and CIAP (calf intestine alkaline phosphatase)-treated λDASHII (Stratagene) at 16° C. overnight, and packaged by Gigapack III gold packaging extract (Stratagene). The packaged extract was infected to *E. coli* XL1Blue MRA(P2) strain and over-laid with NZY medium poured onto LB agar medium. About 8000 plaques were screened using EcoRI-digested pCAT702 as a probe. Six plaques were hybridized to the labeled pCAT702 probe. λDNA was prepared from each λ clone and it was found that 4 of 6 clones contained same fragment to the insert of pCAT702 as a result of PCR using Cat2 and Cat5 primers, and sequencing analysis. A partial nucleotide sequence and its deduced amino acid sequence for CAT gene are listed as SEQ ID NO: 3 and SEQ ID NO: 9 in the sequence listing section.

Example 12

Construction of Disruption Plasmid for the CAT Gene

In a manner similar to Example 7, a disruption plasmid for the CAT gene was constructed. At first, SacI linker was inserted at a HindIII site of pUC19-G418, in which the terminator region of a G418-resistant cassette was located, and as a result of restriction analysis, pUC19-G418Sa, which had a SacI site at the end of the G418-resistant cassette was obtained. Then, a KpnI- and SacI-fragment derived from pUC19-G419Sa was ligated to KpnI- and SacI-digested pCAT702 and yielded pCAT/G706, in which a partial genomic CAT gene was fused to G418-resistant cassette.

Example 13

Transformation of *P. rhodozyma* ATCC 96594 using pCAT/G706 as a Donor

In a similar manner as set forth in Example 8, *P. rhodozyma* ATCC 96594 was transformed with a CAT-disruption plasmid, pCAT/G706. Hundreds of geneticin-resistant clones were yielded after one week of incubation at 20° C. Four of those transformants were selected and the chromosomes were prepared from them. One of the transformants was confirmed to have a disrupted structure of the chromosomal CAT gene by PCR and Southern blot hybridization analyses, and was used for further study.

Subsequently, two candidates for CAT disruptants were characterized with the catalase test, which was often used in bacterial taxonomic study. One loopful of *P. rhodozyma* cells was soaked in 3% $H_2O_2$ solution and the occurrence of dioxygen gas was observed. Although the immediate occurrence of $O_2$ foam was confirmed when ATCC 96594 cells were applied to this catalase test, $O_2$ foam occurred after a long lag when two ATCC 96594 :: pCAT/G706 mutants were soaked in $H_2O_2$ solution. From this result, the disruption of the CAT gene was suggested, but the remaining weak activity indicated the presence of another player who catalyzes the disappearance of $H_2O_2$ such as peroxidase in *P. rhodozyma*.

Example 14

Evaluation of SOD1, SOD2 and CAT Disruptants Derived from *P. rhodozyma* for their Astaxanthin Production The effect of gene disruption of SOD1, SOD2 and CAT gene on astaxanthin production was evaluated by cultivation in YPD medium with shaking flasks. Cells which grew on YPD agar were suspended in YPD medium and a portion of cell suspension was inoculated to 50 ml of YPD medium in 500 ml baffled flask. Cells were grown with 200 rpm at 20° C. for 84 hours. At an appropriate interval, 3 ml of broth was withdrawn and was analyzed for cell yield, consumption of glucose and astaxanthin content.

Cell yield was measured as optical density at 660 nm and as dry cell weight by weighing cells after filtration through 0.45 µm cellulose acetate plus nitrocellulose membrane (HAWP04700, Millipore, Bedford, U.S.A.) and heating at 80° C. overnight. Astaxanthin content of *P. rhodozyma* was measured with HPLC method after extraction of carotenoids from cells of *P. rhodozyma* by disruption with glass beads. After extraction, 5 ml of a mixture containing acetone/BHT/water containing appropriate concentration of bixin as an internal standard was added. Supernatant was analyzed for astaxanthin content with the following HPLC system. HPLC column; YMC-Pak ODS-A (6 mm, 150 mm) Temperature; room temperature Eluent; acetonitrile/methanol/isopropanol (85/10/5) Injection volume; 10 µl Flow Rate; 2.0 ml/minute Detection; UV at 471 nm Results obtained from 84 hour-culture are summarized in TABLE 4.

TABLE 4

The effect of SOD and CAT mutation on the productivity of total carotenoids and astaxanthin by *P. rhodozyma*

| Strain | Total carotenoids (mg/g-dry-cell) | astaxanthin (mg/g-dry cell) |
|---|---|---|
| ATCC 96594 | 0.169 | 0.111 |
| ΔSOD1 | 0.259 | 0.146 |
| ΔSOD2 | 0.202 | 0.129 |
| ΔCAT | 0.229 | 0.144 |

SOD1 and SOD2 disruptants showed elevated level of productivity for total carotenoids as well as astaxanthin compared to their host strain, ATCC 96594. Especially, SOD1 disruptant showed significant increase of carotenoids and astaxanthin production by 53.3% and 31.5%, respectively.

SOD1 seemed to be a mitochondrial enzyme judged from deduced transit peptide sequence at its amino terminal end and might act to scavenge superoxide radical, a kind of active oxygen species occurred in the respiratory chain at mitochondria. These data suggested that astaxanthin production was stimulated by a generation of intracellular active oxygen to compensate the lack of native player of active oxygen species-quenching factor, SOD1.

The invention being thus described, it will be obvious that the same may be varied in many ways. Such variations are not to be regarded as a departure from the spirit and scope of the invention and all such modifications are intended to be included within the scope of the following claims.

What is claimed is:

1. A recombinant polynucleotide sequence comprising a polynucleotide selected from the group consisting of SEQ ID NOs: 1 and 4, and a polynucleotide that hybridizes to the complement of SEQ ID NOs: 1 or 4 under high stringency hybridization and wash conditions, wherein said polynucleotide encodes a polypeptide having mitochondrial superoxide dismutase (SOD) activity.

2. A recombinant polynucleotide sequence according to claim 1 wherein the polynucleotide comprises SEQ ID NO: 1 or SEQ ID NO: 4.

3. A recombinant polynucleotide sequence according to claim 2 wherein the polynucleotide is SEQ ID NO: 1.

4. A recombinant polynucleotide sequence according to claim 2 wherein the polynucleotide is SEQ ID NO: 4.

5. A vector comprising a polynucleotide selected from the group consisting of SEQ ID NOs: 1 and 4, and a polynucleotide that hybridizes to the complement of SEQ ID NOs: 1 or 4 under high stringency hybridization and wash conditions, wherein said polynucleotide encodes a polypeptide having mitochondrial superoxide dismutase (SOD) activity.

6. A vector according to claim 5 wherein the polynucleotide comprises SEQ ID NO: 1 or SEQ ID NO: 4.

7. A vector according to claim 5 wherein the polynucleotide is SEQ ID NO: 1.

8. A vector according to claim 5 wherein the polynucleotide is SEQ ID NO: 4.

9. A disruption cassette for disrupting a polynucleotide selected from the group consisting of SEQ ID NOs: 1 and 4, and a sequence that hybridizes to the complement of SEQ ID NOs: 1 or 4 under high stringency hybridization and wash conditions and encodes a polypeptide having mitochondrial superoxide dismutase (SOD) activity the disruption cassette comprising a selectable marker and a fragment of the polynucleotide.

10. A disruption cassette according to claim 9 wherein the disrupted polynucleotide is in an organism belonging to a kingdom selected from the group consisting of *Monera, Protista* and *Fungi*.

11. A disruption cassette according to claim 10 wherein the organism belongs to a genus selected from the group consisting of *Erwinia, Rhodobacter, Myxococcus, Flavobacter, Paracoccus, Synechococcus, Synechocystis,*

*Agrobacterium, Streptomyces, Haematococcus, Dunaliella, Phaffia, Xanthophyllomyces, Neurospora, Rhodotorula, Blakeslea,* and *Phycomyces.*

12. A disruption cassette according to claim 9 wherein the polynucleotide comprises SEQ ID NO: 1 or SEQ ID NO: 4.

13. A disruption cassette according to claim 12 wherein the polynucleotide is SEQ ID NO: 1.

14. A disruption cassette according to claim 12 wherein the polynucleotide is SEQ ID NO: 4.

15. A vector comprising a disruption cassette according to claim 9.

16. A disruption cassette for disrupting a polynucleotide in a microorganism, which disruption cassette comprises a selectable marker and a fragment of a polynucleotide that is selected from the group consisting of SEQ ID NOs: 1 and 4, and a polynucleotide that hybridizes to the complement of SEQ ID NOs: 1 or 4 under high stringency hybridization and wash conditions, wherein said polynucleotide encodes a polypeptide having mitochondrial superoxide dismutase (SOD) activity.

17. A recombinant organism for producing carotenoids comprising at least one polynucleotide disrupted with a disruption cassette specific to the polynucleotide, wherein the recombinant organism belongs to the kingdom of *Monera, Protista* or *Fungi* and the polynucleotide is selected from the group complement of SEQ ID NOs: 1 or 4 under high stringency hybridization and wash consisting of SEQ ID NOs: 1 and 4, and a polynucleotide that hybridizes to the conditions, wherein said polynucleotide encodes a polypeptide having mitochondrial superoxide dismutase (SOD) activity.

18. A recombinant organism according to claim 17 wherein the recombinant organism belongs to a genus selected from the group consisting of *Erwinia, Rhodobacter, Myxococcus, Flavobacter, Paracoccus, Synechococcus, Synechocystis, Agrobacterium, Streptomyces, Haematococcus, Dunaliella, Phaffia, Xanthophyllomyces, Neurospora, Rhodotorula, Blakeslea,* and *Phycomyces.*

19. A recombinant organism according to claim 17 wherein the polynucleotide comprises SEQ ID NO: 1 or SEQ ID NO: 4.

20. A recombinant organism according to claim 19 wherein the polynucleotide is SEQ ID NO: 1.

21. A recombinant organism according to claim 19 wherein the polynucleotide is SEQ ID NO: 4.

22. A recombinant microorganism for producing carotenoids comprising at least one polynucleotide disrupted with a disruption cassette, which polynucleotide is selected from the group consisting of SEQ ID NOs: 1 and 4, and a polynucleotide that hybridizes to the complement of SEQ ID NOs: 1 or 4 under high stringency hybridization and wash conditions, wherein said polynucleotide encodes a polypeptide having mitochondrial superoxide dismutase (SOD) activity.

23. A process for producing carotenoids comprising cultivating in a culture medium a carotenoid producing recombinant organism containing at least one polynucleotide that is disrupted with a disruption cassette specific to the polynucleotide, wherein the recombinant organism belongs to the kingdom of *Monera, Protista* or *Fungi* and the polynucleotide is selected from the group consisting of SEQ ID NOs: 1 and 4, and a polynucleotide that hybridizes to the complement of SEQ ID NOs: 1 or 4 under high stringency hybridization and wash conditions, wherein said polynucleotide encodes a polypeptide having mitochondrial superoxide dismutase (SOD) activity and recovering carotenoids from the culture.

24. A process according to claim 23 wherein the recombinant organism belongs to a genus selected from the group consisting of *Erwinia, Rhodobacter, Myxococcus, Flavobacter, Paracoccus, Synechococcus, Synechocystis, Agrobacterium, Streptomyces, Haematococcus, Dunaliella, Phaffia, Xanthophyllomyces, Neurospora, Rhodotorula, Blakeslea,* and *Phycomyces.*

25. A process according to claim 24 wherein the recombinant organism is a strain of *P. rhodozyma.*

26. A process according to claim 25 wherein the recombinant organism is *P. rhodozyma* ATCC 98594.

27. A process according to claim 23 wherein the polynucleotide is SEQ ID NO: 1.

28. A process according to claim 23 wherein the polynucleotide comprises SEQ ID NO: 1 or SEQ ID NO: 4.

29. A process according to claim 23 wherein the polynucleotide is SEQ ID NO: 4.

30. A process for producing carotenoids comprising cultivating in a culture medium a carotenoid producing recombinant microorganism containing at least one polynucleotide that is disrupted with a disruption cassette, which polynucleotide is selected from the group consisting of SEQ ID NOs: 1 and 4, and a polynucleotide that hybridizes to the complement or SEQ ID NOs: 1 or 4 under high stringency hybridization and wash conditions, wherein said polynucleotide encodes a polypeptide having mitochondrial superoxide dismutase (SOD) activity and recovering carotenoids from the culture.

31. A method for cloning a polynucleotide encoding a superoxide dismutase comprising providing as a probe or primer a polynucleotide sequence selected from the group consisting of SEQ ID NOs: 1 and 4, and a polynucleotide that hybridizes to the complement of SEQ ID NOs: 1 or 4 under high stringency hybridization and wash conditions, wherein said polynucleotide encodes a polypeptide having mitochondrial superoxide dismutase (SOD) activity.

32. A method according to claim 31 wherein the polynucleotide comprises SEQ ID NO: 1 or SEQ ID NO: 4.

33. A method according to claim 32 wherein the polynucleotide is SEQ ID NO: 1.

34. A method according to claim 32 wherein the polynucleotide is SEQ ID NO: 4.

* * * * *

SEQUENCE LISTING

<160> NUMBER OF SEQ ID NOS: 17

<210> SEQ ID NO 1
<211> LENGTH: 3632
<212> TYPE: DNA
<213> ORGANISM: Phaffia rhodozyma

<400> SEQUENCE: 1

```
tcctgttgat aatctttcta acgccttgta ctttgaccaa ggcgtttgtc cgaaattttg     60
caaacttagt gttggtcgca tggacggtct tcggatccag aactgacggc tcgccaataa    120
agtatgacga tggtagaggt gaaggaggga accacaggtt gaccagtctc aaagagtgct    180
gatgtgcgcg aggatttgtc attaaatggt gttgtatatg ctagagccaa gagaagacat    240
ttggttttgg ttttggtttt gcatttgatg agatgtgtca cgattgaaga cgggaggagg    300
ctcactaacc caagaagcca ggatcaggag gaatgcctcc ccctttcat caagatcttt     360 ctcacatcga acatttgaca ttctctttag tatccttcta tccttttctt ccaacttctc    420
ccattgtatc gactttgctc gacttgctct tcttatctct gagcagagat gggcattcca    480
atatcgaagg agcgacacaa gaccttggag tttgggtaac agatgaagag gggccgaggt    540
ggatggggct gtaggaagta gctgatcgat gagttcctgg atgatgatag gcgaaggaac    600
agacatagga tctctgtctc gtcctggaat tactgagtct tgtatccagc gtgttcttgt    660
ctcgaagaag ccttcaagat cgatgtaaga taagacaggc aatgaggacg gacgaacgaa    720
cgaacgaaaa gaacagaaga gctggtaagt cagtcagtca gtcagtcagt caatcaaaca    780
ctggtgtcta gggttatagc tcgacgcgac gcgacgcgtt tgagacgcga tatgcttacg    840
taatacctgg cgtcatcccc ccagccgagg caagagccga gccgctcgtg aacgacaaaa    900
ttcaaaaggc tttctccatc ttaagctcat tctcatctaa ccgactcatc tcgttcccat    960
cattcccatc attctaccgc catccatgtc tgttcgagca tccctctctt ccgtgtctag   1020
acagactttc gtcgctcctg ctgcttttcca gatcagggca aagcataccc tgcctgagct   1080
tccttacgct tacgatgtaa gacttttccg tgttctccta ttcgtcgctt tcttggtttt   1140
tttcgtcttc gccctctagc tcttcttcgt cctttctgtc ctgctctttg ttgttgatat   1200
tcagctcgat agactaaccc atctcatctc ctggacattc ttttactgga aacgtatctt   1260
gtccttggtt tttcttggct ttggttgaaa attcctctcc actcaggccc tggagccctc   1320
catctccaag gagatcatga cccttcacca caccaagcac catcagactt atgttaacgg   1380
cctcaacgct gccgaggaga gctactcggc cgctgtgggc aaggaggatg tgcttaccca   1440
ggttaagctt cagtctgtac gtctgaccgt ttttttatcg accggaacgc ctggtgagga   1500
gggagatgaa gtttgatgag cgctcatcgt ctagcacgtt gacccgatca tacaggctct   1560
caagttcaac ggaggaggac acatcaatcg tcagtgtatat tcttcaaact cttgctgagc   1620
aagtcaggtc aagctgactg tttcgctttg tttctgcgga tctatctcat ccttgatttg   1680
gcatgatgaa acagactctc tgttctggaa gaacttggct cccctatgga tccgaggagc    1740
taccctctct gaaggacctc tcaagaaggc tatcgaggaa tcttttggtt ctttcgaggg   1800
tccgtccatc tatcttccta ttcagttgtg tttggttccg gtatactcat ctgttttgtt    1860
tccccacaaa ataaaaataa aaatcttgtc ctctccgggg gttcgactgc acgttcatag   1920
ccttcaagaa gaagttcaac gctgacaccg ctgctgtcca aggatccgga tggggctggc   1980
ttgtatgtat catatccttt ccatctcaaa ctcttctcag agtctttttc cttgagactt   2040
```

-continued

| | |
|---|---|
| caaactgact atacatgttt ctacaacaaa caacagggct tgaacccgct tactaagaag | 2100 |
| ctggaagtca ccacgaccgc caaccaggac cctctgctta gtaagttgtt tctacatgat | 2160 |
| tttctatctc aacgcgatct gcatgattcg tcactgattc actggattct cttgtttcgt | 2220 |
| ttttctcggg atgatttcat aaacagctca cattcctatc atcggagttg acgtgcgtat | 2280 |
| cttcttgaa tagtcgtagc gtctgatctc gttttattga ctgacgtgtt gcttctgtcc | 2340 |
| aaatcattaa aaaaaatgaa aacaaataat cgattgaccg acgaaaacag atctgggagc | 2400 |
| acgctttcta ccttcagtac aagaacgtca agcctgacta tctcgctgct gtttggtccg | 2460 |
| ttatcaacta caaggaggca gaggcccgat tgcaggctgc tctctaagcg ggacgaaaag | 2520 |
| taacgacata tgaagggagg atcaaatatc gtttcttcat aaacaacttt cgaggcagat | 2580 |
| gggagagtac gtacaagaga ggtttgtatg gagaattgag tttgttgacg gttagcaggt | 2640 |
| tatgatatat gtagctatag tctagtctaa atctgaaaga agagaacaag atggtttgtc | 2700 |
| cgaagagatt gagagatcaa gcccggtcat ctgatgtcga acaaacatgc cctggtctgc | 2760 |
| caacagtttc tagcacatta tgaccatgtt catgtgtaaa ttgggaaatg agccagaaag | 2820 |
| gtttattatc taattcattg attcatgcga ctatggatac atatgggatt ccagaacaa | 2880 |
| acagatgcaa caaagcacgg cattttccaa agatcgagtc ctcccacaag tatgcggcaa | 2940 |
| ggtttgttgt taagagatat aaaagcagac gacaaaacaa atcgtttatc gaccctgtgc | 3000 |
| accaacaccg tgaccgtttg acgagttggt agagttgtag ttgttgctgt tcaaggagc | 3060 |
| tccagactgg acgcttccaa gcttcaacaa cttctcggca gcgtcgctgt tcgggaaaag | 3120 |
| aaaaggcaaa aaggaacaga gcgataagca tatgtgattc tctacttctt ataggctctt | 3180 |
| agctcaagtc aactcacatg tctttggcgg taccgaagac gttctcaagc tgctgcttgg | 3240 |
| aagcttttcc gagcttgcca gtaggtccct ggttggagaa aagatgtcg aaggctaagg | 3300 |
| gcgatgaaaa gcatgaagat attagctatc ggcgcgataa agtgtgacg agatgaaaat | 3360 |
| ggagaaaaga tgattcgcac catcgacgac ctcgaccaaa ggaatggagg tgtcaccggc | 3420 |
| cttccacttc ttgtactcct caacgttgac gaagatgacg aagcagtcgg tggccttagc | 3480 |
| ctcgggctcg tagatgctga tgaaacacaa taggtagtag gagaggagaa agagaagatg | 3540 |
| atgagatgtc aggatgcttg cttcactgta gatggaggaa gaagatatgc gaagcaagac | 3600 |
| atacactttg gaaagagctt gaaccattgt ag | 3632 |

<210> SEQ ID NO 2
<211> LENGTH: 3375
<212> TYPE: DNA
<213> ORGANISM: Phaffia rhodozyma

<400> SEQUENCE: 2

| | |
|---|---|
| cttatccttc tgccgctggt ctctgtctgt cgagtgtgtg ggatggtttt ggatatgttc | 60 |
| ctatacgaaa ggtagcgcag agcaaagctg acagtattaa gcaagacaag agcttctttc | 120 |
| tgttgacaga tgaaaggacg aactatgaag ctgtccatgc tccccaaacc gattgacaca | 180 |
| ccgccgtcag gcaacgcaga atttctcact gcttcgacgt cacaccaaca tcgatcctcc | 240 |
| atacctaaaa gcagatcgag acacattgtt ggtcgccatg ttggatggat gtacatcaaa | 300 |
| cccacagcat atatcactca catgtgagaa ctccgtagcc tctaccttct tgtctctcaa | 360 |
| tctgaatgtc tcgttgagag gtggaatgaa tgtttacagt ttgagaagac gaaagaaaga | 420 |
| aagagaagag aagagaggaa tacgtacgac gaagttatca tcgtatggga acttttctaa | 480 |

-continued

| | |
|---|---|
| aaaactgcct atagtagaga cgatctctgg aggaaagctc tgtagtatga tagtgaagag | 540 |
| cgagcaagtc tgggcaagtg catccttcgt ctacaagaaa gagaccagga aatgaaggag | 600 |
| agacgagtaa gcaggtacct accgatattg gatcgttctc tctacccagc gatgccttca | 660 |
| ccacgcgttc tatctcttct tgggatggca gatacatact taacgagagc aatctgatgt | 720 |
| ataccgaact tcgaacggaa tgatcccaga atcctcttga acccttgaac ccttgaaccc | 780 |
| tggaaccaag taccaaccga gcaacacgcc gatacggtcc acaccacaga accacacgcc | 840 |
| ctcgtcatta aggtgggac gcgccgatgc tggttacgtt cggcccaatc cggaagttac | 900 |
| cggcttggac gtgcctgtaa ccatgccctg acggtatttc gccttcagct aactccatct | 960 |
| catctttttc ctttactacc acaacccacc cttgaacctt cttccccggc ttttttacta | 1020 |
| tatccatcta tcaatcatca tggctcctta cactcttccc gacgtaagct taaagtttga | 1080 |
| gctgtgtgtg cttatctcaa tcttggagtt gaactcaccg ttttttgttt ttgcttcctg | 1140 |
| gttttttat cggcatccct ccttttttc ccctcgtggt cgcatatgat ttgctcatca | 1200 |
| atcggcgttt cccatgcatc tttgtcatcc gtttcagctt ccttacgctt acgatgcctt | 1260 |
| ggagccttac atctctaagg gtgagattct tagtcagact gttgttccgg ttcgacacga | 1320 |
| tagctaatcg tctctcgttc ctcaatatga acatgcagaa atcatgatcc ttcaccactc | 1380 |
| caagcaccat cagacttacg tcgtacgtaa tctaaaggtc atctccgtct acatggccgg | 1440 |
| atcaacttgc tcatagatct tccttctgtt cggcgctacg tagaccaacc tcaacgccgc | 1500 |
| tatccaggct ttctcccaga ccaatgacat caaggcccag atcgctcttc agagcgctct | 1560 |
| caagttcaac ggaggaggac acatcaaccg tacgatcatt ctccctcttc tggcttatca | 1620 |
| tatgtgttgc ttgtcactaa cacgcatgca accccgggat atctcaccct gtagactccc | 1680 |
| tcttctggaa gaacatggct cctgccgact ctgctgatgc caagctcacc gagggatcgc | 1740 |
| tcaagactgc catcgacaag gactttggat ccttcgagga gttcaagaag aagttcaaca | 1800 |
| ctgctactct cggtgtccag ggatctgtca gtatctcgtt tgcttcgaca tactctcagc | 1860 |
| tttccttccg taaactgacg aatagttttt cggacatgta cttgtaggga tggggatggc | 1920 |
| tcgtgcgttt gaccttttc cactttgaac attagcgata gtgataccta caactgtga | 1980 |
| attggaatat agggatacaa caccgctacc aagcacctcg agatcgccac caccgccaac | 2040 |
| caggatcccc ttatcagtat gtgacttctc tcgtgtggtc accataagcc agttgctgac | 2100 |
| acatttcgtt cgctgtctct cgacttcgta gctttgactc ccatcattgg tcttgacgtt | 2160 |
| agtaattcta tctagtgatt ggagtcgagt tctgaacttg ccttgatctc aaacgaatga | 2220 |
| atcaatttct tttggtagat ctgggagcac gctttctacc tccagtacaa gaatgtcaag | 2280 |
| cctgattacc ttggtacgta attctctatt cgtttgcccc ggtttgatct ttgactcact | 2340 |
| cttcaaaatg ttttcgtttg taactttgaa aaacagccgc tttctggaac gtctgcaact | 2400 |
| ttgctgaggc tcagcgaagg tttgatgtga gtacaggcgc taccccctacg gaggaagcga | 2460 |
| aggtgagctg accactttt atcttctga tttggaatga acgatccgat gatcaaacaa | 2520 |
| acaggctgct gtcaaggctt aatggtccca tttatctctt tgattcgacg gcgatgacgg | 2580 |
| ctttctcgca tccgaagaag gcaaggctat gattactgtt attctgccat gttgcttgct | 2640 |
| ttgctatgct ctatgttctt ttcttttgcc tctcttcaaa gccaaggcgt taaggaaggc | 2700 |
| ccttcagtct gttttacata tgcacatata catgagaaca tatcacggac tcggcggctg | 2760 |
| gtggtccctct tgagcgtcgg cttcaagatt agtgtccaca cgtgaagcgt tcggtgccat | 2820 |
| ccaacctggt aggaatcccc atcgggcggg aatccaatta tcaattggcg gtcggccaga | 2880 |

```
ttcgagctcg ggtatctcag aagcgtcaag cgggcgcatt tccaggcctt taagaggagc    2940
aaatttaatc cgcctgggtg ttcagcgaga cacgaacagt ttgaaacaga gtctgcttgt    3000
gagttactcg gcgagatcac tgaggactaa actttctcag ctcgtggacg aaaagaacga    3060
accaaacggt cttccctgta tctcgaccat ctccttctcc atctcttaca cacctcgga    3120 tgaactccaa ggcttgcttt ccaaagttca aacaaactcc gggttgccat ccacctggtt    3180
tgtctctaac gagccgaggg atatccatcg ttcggaacgt ttgaacagac tggatggtag    3240
gtggccggtc gcttcggaag ccaatcataa tggtgggaat cgagagaagg aatgattggg    3300
cccagtgttt aagacttgtg tttgttggca gagtacggac ggaaagtagg acagacttaa    3360
tcaaggcgag ccaag                                                      3375
```

<210> SEQ ID NO 3
<211> LENGTH: 951
<212> TYPE: DNA
<213> ORGANISM: Phaffia rhodozyma

<400> SEQUENCE: 3

```
tccggaagct cagataccgc tcgagatcct cgaggtttgt gtgctttcgc tttgttcgca    60
tggatgaagc tgttaactta aaaaaatcct cgtgtttctc tttgtttcaa cataggtttc    120
tctcttaagg tcaagacctc tgagggaaac tgggactttg tacgtattct tatcgactga    180
gtcatcaagc tcgttatcgc tctcttaccc tcatccttt gtgtctctgt ctacacctct     240
aggtcggaaa caacactccc atcttttct tgagagaccc agccaagttt ccgatcttca     300
ttcacaccca gaagaggaac ccgcagacaa actctaaaga caaggacgct ttctgggact    360
accgttcgta taaccttgtc actccctgcg tgccgctctg attcatgttg accttgtctt    420
tgatataatt ttatagtatc ccaaaacccc gagtccgtgc atcaggtgct gcacctgttc    480
agtgatcgag gaacccctgc ttcttaccga cacatgcatg gttactctgg acacaccttc    540
aagatggtca acaggaacgg tgactggaat tatgtccaga ttcacatgcg caccgatcag    600
ggtgtcaaga ctcacaccaa tgaagaggct tcgaaactcg acgcctccaa tcccgattca    660
aacggagacg acttgttcga cgcaatcaag aatggagact ccctagctg acggttcag     720 gtacaggtaa tgtctcctga gcaggcccag aagttcagat acaacattct ggatctcacc    780
aaggtctggt cccacaagga gttcccactt aggacgattg gaaagttcac tttgaaccga    840
aacgtggata actatttcgc agaggttgaa cagctcgcct ttgctccttc ccatctgcct    900
cctggaatcg agccctcgaa cgatcccgtc cttcaggctc gactattctc c             951
```

<210> SEQ ID NO 4
<211> LENGTH: 669
<212> TYPE: DNA
<213> ORGANISM: Phaffia rhodozyma
<220> FEATURE:
<221> NAME/KEY: CDS
<222> LOCATION: (1)..(666)
<223> OTHER INFORMATION: n or X = A, C, G or T

<400> SEQUENCE: 4

```
atg tct gtt cga gca tcc ctc tct tcc gtg tct aga cag act ttc gtc       48
Met Ser Val Arg Ala Ser Leu Ser Ser Val Ser Arg Gln Thr Phe Val
1               5                   10                  15 gct cct gct gct ttc cag atc agg gca aag cat acc ctg cct gag ctt       96
Ala Pro Ala Ala Phe Gln Ile Arg Ala Lys His Thr Leu Pro Glu Leu
            20                  25                  30
```

```
cct tac gct tac gat gcc ctg gag ccc tcc atc tcc aag gag atc atg      144
Pro Tyr Ala Tyr Asp Ala Leu Glu Pro Ser Ile Ser Lys Glu Ile Met
         35                  40                  45 acc ctt cac cac acc aag cac cat cag act tat gtt aac ggc ctc aac      192
Thr Leu His His Thr Lys His His Gln Thr Tyr Val Asn Gly Leu Asn
 50                  55                  60 gct gcc gag gag agc tac tcg gcc gct gtg ggc aag gag gat gtg ctt      240
Ala Ala Glu Glu Ser Tyr Ser Ala Ala Val Gly Lys Glu Asp Val Leu
 65                  70                  75                  80 acc cag gtt aag ctt cag tct gct ctc aag ttc aac gga gga gga cac      288
Thr Gln Val Lys Leu Gln Ser Ala Leu Lys Phe Asn Gly Gly Gly His
             85                  90                  95 atc aat cac tct ctg ttc tgg aag aac ttg gct ccc tat gga tcc gag      336
Ile Asn His Ser Leu Phe Trp Lys Asn Leu Ala Pro Tyr Gly Ser Glu
        100                 105                 110 gag gct acc ctc tct gaa gga cct ctc aag aag gct atc gag gaa tct      384
Glu Ala Thr Leu Ser Glu Gly Pro Leu Lys Lys Ala Ile Glu Glu Ser
        115                 120                 125 ttt ggt tct ttc gag gcc ttc aag aag aag ttc aac gct gac acc gct      432
Phe Gly Ser Phe Glu Ala Phe Lys Lys Lys Phe Asn Ala Asp Thr Ala
130                 135                 140 gct gtc caa gga tcc gga tgg ggc tgg ctt ggc ttg aac ccg ctt act      480
Ala Val Gln Gly Ser Gly Trp Gly Trp Leu Gly Leu Asn Pro Leu Thr
145                 150                 155                 160 aag aag ctg gaa gtc acc acg acc gcc aac cag gac cct ctg ctt act      528
Lys Lys Leu Glu Val Thr Thr Thr Ala Asn Gln Asp Pro Leu Leu Thr
                165                 170                 175 cac att cct atc atc gga gtt gac atc tgg gag cac gct ttc tac ctt      576
His Ile Pro Ile Ile Gly Val Asp Ile Trp Glu His Ala Phe Tyr Leu
                180                 185                 190 cag tac aag aac gtc aag cct gac tat ctc gct gct gtt tgg tcc gtt      624
Gln Tyr Lys Asn Val Lys Pro Asp Tyr Leu Ala Ala Val Trp Ser Val
            195                 200                 205 atc aac tac aag gag gca gag gcc cga ttg cag gct gct ctc taa          669
Ile Asn Tyr Lys Glu Ala Glu Ala Arg Leu Gln Ala Ala Leu
210                 215                 220

<210> SEQ ID NO 5
<211> LENGTH: 222
<212> TYPE: PRT
<213> ORGANISM: Phaffia rhodozyma

<400> SEQUENCE: 5

Met Ser Val Arg Ala Ser Leu Ser Ser Val Ser Arg Gln Thr Phe Val
  1               5                  10                  15

Ala Pro Ala Ala Phe Gln Ile Arg Ala Lys His Thr Leu Pro Glu Leu
             20                  25                  30

Pro Tyr Ala Tyr Asp Ala Leu Glu Pro Ser Ile Ser Lys Glu Ile Met
         35                  40                  45

Thr Leu His His Thr Lys His His Gln Thr Tyr Val Asn Gly Leu Asn
 50                  55                  60

Ala Ala Glu Glu Ser Tyr Ser Ala Ala Val Gly Lys Glu Asp Val Leu
 65                  70                  75                  80

Thr Gln Val Lys Leu Gln Ser Ala Leu Lys Phe Asn Gly Gly Gly His
             85                  90                  95

Ile Asn His Ser Leu Phe Trp Lys Asn Leu Ala Pro Tyr Gly Ser Glu
        100                 105                 110

Glu Ala Thr Leu Ser Glu Gly Pro Leu Lys Lys Ala Ile Glu Glu Ser
        115                 120                 125
```

```
Phe Gly Ser Phe Glu Ala Phe Lys Lys Lys Phe Asn Ala Asp Thr Ala
        130                 135                 140
Ala Val Gln Gly Ser Gly Trp Gly Trp Leu Gly Leu Asn Pro Leu Thr
145                 150                 155                 160
Lys Lys Leu Glu Val Thr Thr Thr Ala Asn Gln Asp Pro Leu Leu Thr
                165                 170                 175
His Ile Pro Ile Ile Gly Val Asp Ile Trp Glu His Ala Phe Tyr Leu
                180                 185                 190
Gln Tyr Lys Asn Val Lys Pro Asp Tyr Leu Ala Ala Val Trp Ser Val
            195                 200                 205
Ile Asn Tyr Lys Glu Ala Glu Ala Arg Leu Gln Ala Ala Leu
        210                 215                 220

<210> SEQ ID NO 6
<211> LENGTH: 597
<212> TYPE: DNA
<213> ORGANISM: Phaffia rhodozyma
<220> FEATURE:
<221> NAME/KEY: CDS
<222> LOCATION: (1)..(594)
<223> OTHER INFORMATION:

<400> SEQUENCE: 6 atg gct cct tac act ctt ccc gac ctt cct tac gct tac gat gcc ttg      48
Met Ala Pro Tyr Thr Leu Pro Asp Leu Pro Tyr Ala Tyr Asp Ala Leu
1               5                   10                  15 gag cct tac atc tct aag gaa atc atg atc ctt cac cac tcc aag cac      96
Glu Pro Tyr Ile Ser Lys Glu Ile Met Ile Leu His His Ser Lys His
                20                  25                  30 cat cag act tac gtc acc aac ctc aac gcc gct atc cag gct ttc tcc     144
His Gln Thr Tyr Val Thr Asn Leu Asn Ala Ala Ile Gln Ala Phe Ser
            35                  40                  45 cag acc aat gac atc aag gcc cag atc gct ctt cag agc gct ctc aag     192
Gln Thr Asn Asp Ile Lys Ala Gln Ile Ala Leu Gln Ser Ala Leu Lys
        50                  55                  60 ttc aac gga gga gga cac atc aac cac tcc ctc ttc tgg aag aac atg     240
Phe Asn Gly Gly Gly His Ile Asn His Ser Leu Phe Trp Lys Asn Met
65                  70                  75                  80 gct cct gcc gac tct gct gat gcc aag ctc acc gag gga tcg ctc aag     288
Ala Pro Ala Asp Ser Ala Asp Ala Lys Leu Thr Glu Gly Ser Leu Lys
                85                  90                  95 act gcc atc gac aag gac ttt gga tcc ttc gag gag ttc aag aag aag     336
Thr Ala Ile Asp Lys Asp Phe Gly Ser Phe Glu Glu Phe Lys Lys Lys
            100                 105                 110 ttc aac act gct act ctc ggt gtc cag gga tct gga tgg gga tgg ctc     384
Phe Asn Thr Ala Thr Leu Gly Val Gln Gly Ser Gly Trp Gly Trp Leu
        115                 120                 125 gga tac aac acc gct acc aag cac ctc gag atc gcc acc acc gcc aac     432
Gly Tyr Asn Thr Ala Thr Lys His Leu Glu Ile Ala Thr Thr Ala Asn
130                 135                 140 cag gat ccc ctt atc act ttg act ccc atc att ggt ctt gac atc tgg     480
Gln Asp Pro Leu Ile Thr Leu Thr Pro Ile Ile Gly Leu Asp Ile Trp
145                 150                 155                 160 gag cac gct ttc tac ctc cag tac aag aat gtc aag cct gat tac ctt     528
Glu His Ala Phe Tyr Leu Gln Tyr Lys Asn Val Lys Pro Asp Tyr Leu
                165                 170                 175 gcc gct ttc tgg aac gtc tgc aac ttt gct gag gct cag cga agg ttt     576
Ala Ala Phe Trp Asn Val Cys Asn Phe Ala Glu Ala Gln Arg Arg Phe
            180                 185                 190
```

```
                                                                -continued gat gct gct gtc aag gct taa                                        597
Asp Ala Ala Val Lys Ala
        195

<210> SEQ ID NO 7
<211> LENGTH: 198
<212> TYPE: PRT
<213> ORGANISM: Phaffia rhodozyma

<400> SEQUENCE: 7

Met Ala Pro Tyr Thr Leu Pro Asp Leu Pro Tyr Ala Tyr Asp Ala Leu
1               5                   10                  15

Glu Pro Tyr Ile Ser Lys Glu Ile Met Ile Leu His Ser Lys His
            20                  25                  30

His Gln Thr Tyr Val Thr Asn Leu Asn Ala Ala Ile Gln Ala Phe Ser
        35                  40                  45

Gln Thr Asn Asp Ile Lys Ala Gln Ile Ala Leu Gln Ser Ala Leu Lys
    50                  55                  60

Phe Asn Gly Gly Gly His Ile Asn His Ser Leu Phe Trp Lys Asn Met
65                  70                  75                  80

Ala Pro Ala Asp Ser Ala Asp Ala Lys Leu Thr Glu Gly Ser Leu Lys
                85                  90                  95

Thr Ala Ile Asp Lys Asp Phe Gly Ser Phe Glu Glu Phe Lys Lys Lys
            100                 105                 110

Phe Asn Thr Ala Thr Leu Gly Val Gln Gly Ser Gly Trp Gly Trp Leu
        115                 120                 125

Gly Tyr Asn Thr Ala Thr Lys His Leu Glu Ile Ala Thr Thr Ala Asn
    130                 135                 140

Gln Asp Pro Leu Ile Thr Leu Thr Pro Ile Ile Gly Leu Asp Ile Trp
145                 150                 155                 160

Glu His Ala Phe Tyr Leu Gln Tyr Lys Asn Val Lys Pro Asp Tyr Leu
                165                 170                 175

Ala Ala Phe Trp Asn Val Cys Asn Phe Ala Glu Ala Gln Arg Arg Phe
            180                 185                 190

Asp Ala Ala Val Lys Ala
        195

<210> SEQ ID NO 8
<211> LENGTH: 714
<212> TYPE: DNA
<213> ORGANISM: Phaffia rhodozyma
<220> FEATURE:
<221> NAME/KEY: CDS
<222> LOCATION: (1)..(714)
<223> OTHER INFORMATION:

<400> SEQUENCE: 8 tcc gga agc tca gat acc gct cga gat cct cga ggt ttc tct ctt aag    48
Ser Gly Ser Ser Asp Thr Ala Arg Asp Pro Arg Gly Phe Ser Leu Lys
1               5                   10                  15 gtc aag acc tct gag gga aac tgg gac ttt gtc gga aac aac act ccc    96
Val Lys Thr Ser Glu Gly Asn Trp Asp Phe Val Gly Asn Asn Thr Pro
            20                  25                  30 atc ttt ttc ttg aga gac cca gcc aag ttt ccg atc ttc att cac acc   144
Ile Phe Phe Leu Arg Asp Pro Ala Lys Phe Pro Ile Phe Ile His Thr
        35                  40                  45 cag aag agg aac ccg cag aca aac tct aaa gac aag gac gct ttc tgg   192
Gln Lys Arg Asn Pro Gln Thr Asn Ser Lys Asp Lys Asp Ala Phe Trp
    50                  55                  60
```

```
gac tac cta tcc caa aac ccc gag tcc gtg cat cag gtg ctg cac ctg      240
Asp Tyr Leu Ser Gln Asn Pro Glu Ser Val His Gln Val Leu His Leu
 65              70                  75                  80 ttc agt gat cga gga acc cct gct tct tac cga cac atg cat ggt tac      288
Phe Ser Asp Arg Gly Thr Pro Ala Ser Tyr Arg His Met His Gly Tyr
                 85                  90                  95 tct gga cac acc ttc aag atg gtc aac agg aac ggt gac tgg aat tat      336
Ser Gly His Thr Phe Lys Met Val Asn Arg Asn Gly Asp Trp Asn Tyr
            100                 105                 110 gtc cag att cac atg cgc acc gat cag ggt gtc aag act cac acc aat      384
Val Gln Ile His Met Arg Thr Asp Gln Gly Val Lys Thr His Thr Asn
        115                 120                 125 gaa gag gct tcg aaa ctc gac gcc tcc aat ccc gat tca aac gga gac      432
Glu Glu Ala Ser Lys Leu Asp Ala Ser Asn Pro Asp Ser Asn Gly Asp
    130                 135                 140 gac ttg ttc gac gca atc aag aat gga gac ttc cct agc tgg acg gtt      480
Asp Leu Phe Asp Ala Ile Lys Asn Gly Asp Phe Pro Ser Trp Thr Val
145                 150                 155                 160 cag gta cag gta atg tct cct gag cag gcc cag aag ttc aga tac aac      528
Gln Val Gln Val Met Ser Pro Glu Gln Ala Gln Lys Phe Arg Tyr Asn
                165                 170                 175 att ctg gat ctc acc aag gtc tgg tcc cac aag gag ttc cca ctt agg      576
Ile Leu Asp Leu Thr Lys Val Trp Ser His Lys Glu Phe Pro Leu Arg
            180                 185                 190 acg att gga aag ttc act ttg aac cga aac gtg gat aac tat ttc gca      624
Thr Ile Gly Lys Phe Thr Leu Asn Arg Asn Val Asp Asn Tyr Phe Ala
        195                 200                 205 gag gtt gaa cag ctc gcc ttt gct cct tcc cat ctg cct cct gga atc      672
Glu Val Glu Gln Leu Ala Phe Ala Pro Ser His Leu Pro Pro Gly Ile
    210                 215                 220 gag ccc tcg aac gat ccc gtc ctt cag gct cga cta ttc tcc              714
Glu Pro Ser Asn Asp Pro Val Leu Gln Ala Arg Leu Phe Ser
225                 230                 235

<210> SEQ ID NO 9
<211> LENGTH: 238
<212> TYPE: PRT
<213> ORGANISM: Phaffia rhodozyma

<400> SEQUENCE: 9

Ser Gly Ser Ser Asp Thr Ala Arg Asp Pro Arg Gly Phe Ser Leu Lys
 1               5                  10                  15

Val Lys Thr Ser Glu Gly Asn Trp Asp Phe Val Gly Asn Asn Thr Pro
                20                  25                  30

Ile Phe Phe Leu Arg Asp Pro Ala Lys Phe Pro Ile Phe Ile His Thr
            35                  40                  45

Gln Lys Arg Asn Pro Gln Thr Asn Ser Lys Asp Lys Asp Ala Phe Trp
        50                  55                  60

Asp Tyr Leu Ser Gln Asn Pro Glu Ser Val His Gln Val Leu His Leu
 65              70                  75                  80

Phe Ser Asp Arg Gly Thr Pro Ala Ser Tyr Arg His Met His Gly Tyr
                85                  90                  95

Ser Gly His Thr Phe Lys Met Val Asn Arg Asn Gly Asp Trp Asn Tyr
            100                 105                 110

Val Gln Ile His Met Arg Thr Asp Gln Gly Val Lys Thr His Thr Asn
        115                 120                 125

Glu Glu Ala Ser Lys Leu Asp Ala Ser Asn Pro Asp Ser Asn Gly Asp
    130                 135                 140
```

```
Asp Leu Phe Asp Ala Ile Lys Asn Gly Asp Phe Pro Ser Trp Thr Val
145                 150                 155                 160

Gln Val Gln Val Met Ser Pro Glu Gln Ala Gln Lys Phe Arg Tyr Asn
                165                 170                 175

Ile Leu Asp Leu Thr Lys Val Trp Ser His Lys Glu Phe Pro Leu Arg
            180                 185                 190

Thr Ile Gly Lys Phe Thr Leu Asn Arg Asn Val Asp Asn Tyr Phe Ala
        195                 200                 205

Glu Val Glu Gln Leu Ala Phe Ala Pro Ser His Leu Pro Pro Gly Ile
    210                 215                 220

Glu Pro Ser Asn Asp Pro Val Leu Gln Ala Arg Leu Phe Ser
225                 230                 235

<210> SEQ ID NO 10
<211> LENGTH: 23
<212> TYPE: DNA
<213> ORGANISM: Artificial Sequence
<220> FEATURE:
<223> OTHER INFORMATION: Sod1 (sense primer for cloning of SOD genes)
<221> NAME/KEY: misc_feature
<222> LOCATION: (1)..(23)
<223> OTHER INFORMATION: n or X = A, C, G or T

<400> SEQUENCE: 10
aarcaycayc aracntaygt naa                                          23

<210> SEQ ID NO 11
<211> LENGTH: 23
<212> TYPE: DNA
<213> ORGANISM: Artificial Sequence
<220> FEATURE:
<223> OTHER INFORMATION: Sod4 (antisense primer for cloning of SOD
      genes)
<221> NAME/KEY: misc_feature
<222> LOCATION: (1)..(23)
<223> OTHER INFORMATION: n or X = A, C, G or T

<400> SEQUENCE: 11
gcccanccng anccytgnac ncc                                          23

<210> SEQ ID NO 12
<211> LENGTH: 26
<212> TYPE: DNA
<213> ORGANISM: Artificial Sequence
<220> FEATURE:
<223> OTHER INFORMATION: Sod14 (sense primer for the construction of
      SOD1--disrupting plasmid)

<400> SEQUENCE: 12
ggtacctccg atgataggaa tgtgag                                       26

<210> SEQ ID NO 13
<211> LENGTH: 26
<212> TYPE: DNA
<213> ORGANISM: Artificial Sequence
<220> FEATURE:
<223> OTHER INFORMATION: Sod15 (antisense primer for the construction of
      SOD1-disrupting plasmid)

<400> SEQUENCE: 13
gaattcagtt caacggagga ggacac                                       26

<210> SEQ ID NO 14
<211> LENGTH: 26
<212> TYPE: DNA
```

-continued

```
<213> ORGANISM: Artificial Sequence
<220> FEATURE:
<223> OTHER INFORMATION: Sod47 (sense primer for the contruction of
      SOD2-disrupting plasmid)

<400> SEQUENCE: 14
gaattcggag gaggacacat caaccg                                          26

<210> SEQ ID NO 15
<211> LENGTH: 26
<212> TYPE: DNA
<213> ORGANISM: Artificial Sequence
<220> FEATURE:
<223> OTHER INFORMATION: Sod48 (antisense primer for the construction of
      SOD2-disrupting plasmid)

<400> SEQUENCE: 15
ggtacctgta ctggaggtag aaagcg                                          26

<210> SEQ ID NO 16
<211> LENGTH: 23
<212> TYPE: DNA
<213> ORGANISM: Artificial Sequence
<220> FEATURE:
<223> OTHER INFORMATION: Sod2 (sense primer for cloning of CAT gene)
<221> NAME/KEY: misc_feature
<222> LOCATION: (1)..(23)
<223> OTHER INFORMATION: n or X = A, C, G or T

<400> SEQUENCE: 16
mgnttytcna cngtnggngg nga                                             23

<210> SEQ ID NO 17
<211> LENGTH: 23
<212> TYPE: DNA
<213> ORGANISM: Artificial Sequence
<220> FEATURE:
<223> OTHER INFORMATION: Cat5 (antisense primer for cloning of CAT gene)
<221> NAME/KEY: misc_feature
<222> LOCATION: (1)..(23)
<223> OTHER INFORMATION: n or X = A, C, G or T

<400> SEQUENCE: 17
ckrtgnckyt gngtrtcngg rta                                             23
```